(12) United States Patent
Suzuki et al.

(10) Patent No.: US 8,815,887 B2
(45) Date of Patent: Aug. 26, 2014

(54) PROPHYLACTIC OR THERAPEUTIC METHOD FOR SJOGREN'S SYNDROME

(71) Applicant: Takeda Pharmaceutical Company Limited, Osaka (JP)

(72) Inventors: Nobutaka Suzuki, Kanagawa (JP); Takahiro Miyazaki, Kanagawa (JP); Takashi Ochi, Kanagawa (JP)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/095,026

(22) Filed: Dec. 3, 2013

(65) Prior Publication Data
US 2014/0155437 A1 Jun. 5, 2014

Related U.S. Application Data

(60) Provisional application No. 61/733,176, filed on Dec. 4, 2012, provisional application No. 61/894,641, filed on Oct. 23, 2013.

(51) Int. Cl.
- *A61K 31/435* (2006.01)
- *A61K 31/44* (2006.01)
- *C07D 213/89* (2006.01)

(52) U.S. Cl.
CPC ................. *C07D 213/89* (2013.01)
USPC ......................... 514/277; 514/358

(58) Field of Classification Search
CPC ................. A61K 31/44; A61K 31/4412
USPC ........................... 514/277, 358
See application file for complete search history.

(56) References Cited

U.S. PATENT DOCUMENTS

| 6,939,885 B2 | 9/2005 | Ungashe et al. |
| 7,238,717 B2 | 7/2007 | Fleming et al. |

(Continued)

FOREIGN PATENT DOCUMENTS

| WO | WO 03/099773 A1 | 12/2003 |
| WO | WO 2004/046092 A2 | 6/2004 |

(Continued)

OTHER PUBLICATIONS

Fox, Robert J., "Sjögren's syndrome," Lancet, Jul. 23, 2005, 366:321-331.

(Continued)

*Primary Examiner* — San-Ming Hui
(74) *Attorney, Agent, or Firm* — Foley & Lardner LLP

(57) ABSTRACT

The present invention provides a prophylactic or therapeutic agent and a prophylactic or therapeutic method superior in the prophylaxis or treatment of Sjogren's syndrome. Provided are a prophylactic or therapeutic agent for Sjogren's syndrome, containing a compound represented by the formula (I):

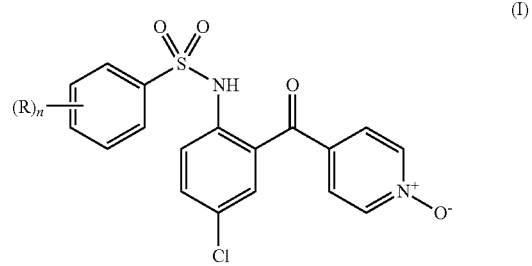

wherein each symbol is as defined in the Specification, or a pharmaceutically acceptable salt thereof, and a method for the prophylaxis or treatment of Sjogren's syndrome, including administering an effective amount of the compound represented by the formula (I) or a pharmaceutically acceptable salt thereof, to a subject in need thereof.

4 Claims, 8 Drawing Sheets

Mean+/-SEM (N=25-27)
*: p<0.025 vs Vehicle control group (one-tailed Williams' test)

(56) References Cited

U.S. PATENT DOCUMENTS

| | | |
|---|---|---|
| 7,759,390 B2 | 7/2010 | Carballido Herrera et al. |
| 7,781,481 B2 | 8/2010 | Carballido Herrera et al. |
| 8,168,673 B2 | 5/2012 | Armer et al. |
| 2004/0038976 A1 | 2/2004 | Fleming et al. |
| 2004/0171654 A1 | 9/2004 | Ugashe et al. |
| 2008/0269312 A1 | 10/2008 | Carballido Herrera et al. |
| 2008/0275114 A1 | 11/2008 | Carballido Herrera et al. |
| 2008/0300295 A1 | 12/2008 | Carballido Herrera et al. |
| 2008/0312313 A1 | 12/2008 | Carballido Herrera et al. |
| 2009/0186923 A1 | 7/2009 | Armer et al. |
| 2009/0192195 A1 | 7/2009 | Armer et al. |
| 2010/0022613 A1 | 1/2010 | Armer et al. |
| 2010/0075963 A1 | 3/2010 | Lehr et al. |
| 2013/0225580 A1 | 8/2013 | Chen et al. |

FOREIGN PATENT DOCUMENTS

| | | |
|---|---|---|
| WO | WO 2007/071440 A1 | 6/2007 |
| WO | WO 2007/071441 A1 | 6/2007 |
| WO | WO 2007/071442 A2 | 6/2007 |
| WO | WO 2007/071443 A1 | 6/2007 |
| WO | WO 2008/095908 A1 | 8/2008 |
| WO | WO 2009/090414 A1 | 7/2009 |
| WO | WO 2009/093026 A1 | 7/2009 |
| WO | WO 2009/093029 A1 | 7/2009 |
| WO | WO 2013/130811 A1 | 9/2013 |

OTHER PUBLICATIONS

Hansen et al., "Dysregulation of Chemokine Receptor Expression and Function by B Cells of Patients with Primary Sjögren's Syndrome," Arthritis & Rheumatism, Jul. 2005, 21(7):2109-2119.

Kunkel et al., "Lymphocyte CC Chemokine Receptor 9 and Epithelial Thymus-expresses Chemokine (TECK) Expression Distinguish the Small Intestinal Immune Compartment: Epithelial Expression of Tissue-specific Chemokines as an Organizing Principle in Regional Immunity," J. Exp. Med., Sep. 4, 2000, 192(5):761-767.

Lavoie et al., "Current Concepts: Mouse Models of Sjögren's Syndrome," Journal of Biomedicine and Biotechnology, 2011, Article ID 549107, 14 pages, published online Dec. 30, 2010.

Lisi et al., "Sjögren's syndrome autoantibodies provoke changes in gene expression profiles of inflammatory cytokines triggering a pathway involving TACE/NF-κB," Laboratory Investigation, 2012, 92:615-624.

McGuire et al., "A Subset of Interleukin-21$^+$ Chemokine Receptor CCR9$^+$ T Helper Cells Target Accessory Organs of the Digestive System in Autoimmunity," Immunity, Apr. 22, 2011, 34:602-615.

Mean+/-SEM (N=25-27)

*: p<0.025 vs Vehicle control group (one-tailed Williams' test)

Mean+/-SEM (N=21-26)

*: $p<0.025$ vs Vehicle control group (one-tailed Williams' test)

Mean+/-SEM (N=12-19)

Compound A group; *: P<0.025 vs Vehicle (one-tailed Williams' test)

Compound B group; #: P<0.05 vs Vehicle (Dunnett's test)

*: vs Vehicle at P<0.025 (one-tailed Williams' test)
**: vs Vehicle at P<0.005 (one-tailed Williams' test)

*vs Vehicle at P<0.05
(Fisher's exact test)

| Route, dose | p.o., 50 mg/kg b.i.d. | | | p.o., 250 mg/kg b.i.d. | | |
|---|---|---|---|---|---|---|
| | 0 - 8 h | 8 - 24 h | 0 - 24 h | 0 - 8 h | 8 - 24 h | 0 - 24 h |
| $C_{max}$ (µg/mL) | 4.506 | 6.001 | 6.001 | 11.653 | 13.266 | 13.266 |
| $T_{max}$ (h) | 0.50 | 9.00 | 9.00 | 1.00 | 9.00 | 9.00 |
| AUC (µg·h/mL) | 11.415 | 17.001 | 28.416 | 53.323 | 46.423 | 99.746 |

(n = 3 x 2 groups)

| Route, dose | p.o., 50 mg/kg b.i.d. | | | p.o., 250 mg/kg b.i.d. | | |
|---|---|---|---|---|---|---|
| | 0 - 8 h | 8 - 24 h | 0 - 24 h | 0 - 8 h | 8 - 24 h | 0 - 24 h |
| $C_{max}$ (μg/mL) | 0.693 | 1.542 | 1.542 | 2.492 | 2.137 | 2.492 |
| $T_{max}$ (h) | 0.25 | 8.25 | 8.25 | 0.25 | 8.50 | 0.25 |
| AUC (μg·h/mL) | 1.352 | 2.052 | 3.404 | 4.035 | 5.717 | 9.752 |

(n = 3 x 2 groups)

PROPHYLACTIC OR THERAPEUTIC METHOD FOR SJOGREN'S SYNDROME

TECHNICAL FIELD OF THE INVENTION

The present invention relates to a prophylactic or therapeutic agent and a prophylactic or therapeutic method for Sjogren's syndrome.

BACKGROUND OF THE INVENTION

Sjogren's syndrome is a chronic inflammatory autoimmune disease in which the exocrine organs, mainly the salivary and lacrimal glands, undergo progressive destruction by lymphocytes resulting in causing the typical sicca symptoms such as dry eye and dry mouth by decreased production of saliva and tears, but is the cause of this is uncertain. It has been reported that patients with Sjogren's syndrome present broad spectrum analytical features including hypergammaglobulinemia, and autoantibodies including anti-SS-A/Ro and anti-SS-B/La antibodies, and also the incidence of malignant lymphoma is high in the Sjogren's syndrome patients (Fox R I, Lancet. 2005; 366: 321-31).

The main therapeutic method of Sjogren's syndrome is based on symptomatic treatment of sicca features. For symptomatic therapy of dry eye, eye drops and glasses for preventing flow of lacrimal fluid are used, and for symptomatic therapy of dry mouth, artificial saliva and mouth cavity washing are used. While a treatment for improving xerostomia by the use of muscarinic acetylcholine receptor agonist (i.e., cevimeline) for patients with residual salivary gland function is also available, but its beneficial effect is limited. Therefore, the development of new effective and highly selective therapies for Sjogren's syndrome is desired.

Patent document 1 discloses a compound represented by a formula encompassing N-{4-chloro-2-[(1-oxidopyridin-4-yl)carbonyl]phenyl}-4-(propan-2-yloxy)benzenesulfonamide, and teaches that the compound inhibits CCR9 receptor function. However, this document does not describe that the compound can be used for the prophylaxis or treatment of Sjogren's syndrome.

Patent document 2 discloses a compound represented by a formula encompassing N-{4-chloro-2-[(1-oxidopyridin-4-yl)carbonyl]phenyl}-4-(tert-butyl)benzenesulfonamide, and teaches that the compound acts as a CCR9 antagonist. However, this document does not describe that the compound can be used for the prophylaxis or treatment of Sjogren's syndrome.

DOCUMENT LIST

Patent Documents patent document 1: WO2003/099773
patent document 2: WO2004/046092

SUMMARY OF THE INVENTION

Problems to be Solved by the Invention

The present invention aims to provide a novel prophylactic or therapeutic agent and a prophylactic or therapeutic method for Sjogren's syndrome.

Means of Solving the Problems

The present inventors have conducted intensive studies in an attempt to solve the aforementioned problems and found that a compound represented by the below-mentioned formula (I) or a pharmaceutically acceptable salt thereof is unexpectedly useful for the prophylaxis or treatment of Sjogren's syndrome, and conducted further studies based on the finding, which resulted in the completion of the present invention.

Accordingly, the present invention provides the following.

[1] A prophylactic or therapeutic agent for Sjogren's syndrome, comprising a compound represented by the formula (I):

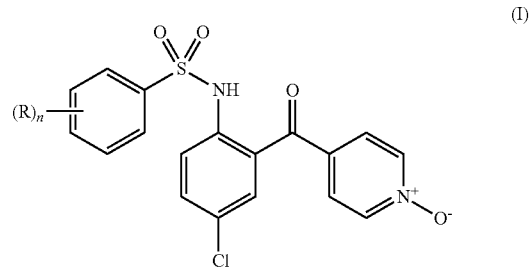

wherein n is an integer of 1-3;
R is each independently an aliphatic group, haloalkyl, aryl, arylalkyl, alkoxy, cycloalkoxy, haloalkoxy, aryloxy, arylalkoxy, alkylthio, a halogen atom, nitro, cyano, hydroxy, $NR^1CO_2R^2$, $C(O)N(R^1)_2$, $C(O)R^2$, $CO_2R^2$, $OC(O)N(R^1)_2$, $OC(O)R^2$, $N(R^1)_2$ or $NR^1C(O)R^2$; or two adjacent R groups form, together with an atom bonded thereto, a condensed, saturated, unsaturated, or partially unsaturated 5- to 7-membered ring having 0, 1 or 2 hetero atoms selected from N, O and S;
$R^1$ is each independently a hydrogen atom or an aliphatic group; and
$R^2$ is an aliphatic group
(hereinafter sometimes referred to as compound (I)) or a pharmaceutically acceptable salt thereof.
[2] The agent of the above-mentioned [1], wherein R is an aliphatic group, alkoxy or haloalkoxy.
[3] The agent of the above-mentioned [1], wherein the compound represented by the formula (I) is N-{4-chloro-2-[(1-oxidopyridin-4-yl)carbonyl]phenyl}-4-(propan-2-yloxy) benzenesulfonamide (hereinafter sometimes referred to as compound A).
[4] The agent of the above-mentioned [1], wherein the compound represented by the formula (I) is N-{4-chloro-2-[(1-oxidopyridin-4-yl)carbonyl]phenyl}-4-(tert-butyl)benzenesulfonamide (hereinafter sometimes referred to as compound B).
[5] A method for the prophylaxis or treatment of Sjogren's syndrome, comprising administering an effective amount of a compound represented by the formula (I):

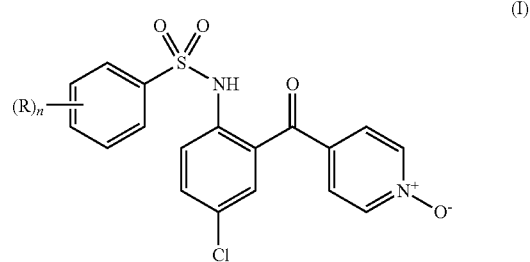

wherein n is an integer of 1-3;
R is each independently an aliphatic group, haloalkyl, aryl, arylalkyl, alkoxy, cycloalkoxy, haloalkoxy, aryloxy, arylalkoxy, alkylthio, a halogen atom, nitro, cyano, hydroxy, $NR^1CO_2R^2$, $C(O)N(R^1)_2$, $C(O)R^2$, $CO_2R^2$, $OC(O)N(R^1)_2$, $OC(O)R^2$, $N(R^1)_2$ or $NR^1C(O)R^2$; or two adjacent R groups form, together with an atom bonded thereto, a condensed, saturated, unsaturated, or partially unsaturated 5- to 7-membered ring having 0, 1 or 2 hetero atoms selected from N, O and S;
$R^1$ is each independently a hydrogen atom or an aliphatic group; and
$R^2$ is an aliphatic group,
or a pharmaceutically acceptable salt thereof, to a subject in need thereof.

[6] The method of the above-mentioned [5], wherein R is an aliphatic group, alkoxy or haloalkoxy.

[7] The method of the above-mentioned [5], wherein the compound represented by the formula (I) is N-{4-chloro-2-[(1-oxidopyridin-4-yl)carbonyl]phenyl}-4-(propan-2-yloxy)benzenesulfonamide.

[8] The method of the above-mentioned [5], wherein the compound represented by the formula (I) is N-{4-chloro-2-[(1-oxidopyridin-4-yl)carbonyl]phenyl}-4-(tert-butyl)benzenesulfonamide.

[9] A compound represented by the formula (I):

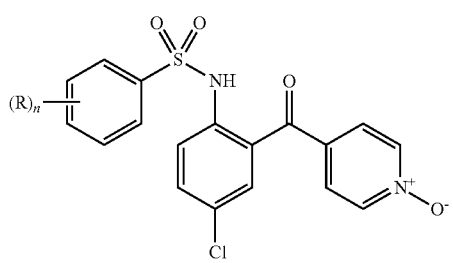

wherein n is an integer of 1-3;
R is each independently an aliphatic group, haloalkyl, aryl, arylalkyl, alkoxy, cycloalkoxy, haloalkoxy, aryloxy, arylalkoxy, alkylthio, a halogen atom, nitro, cyano, hydroxy, $NR^1CO_2R^2$, $C(O)N(R^1)_2$, $C(O)R^2$, $CO_2R^2$, $OC(O)N(R^1)_2$, $OC(O)R^2$, $N(R^1)_2$ or NR $C(O)R^2$; or two adjacent R groups form, together with an atom bonded thereto, a condensed, saturated, unsaturated, or partially unsaturated 5- to 7-membered ring having 0, 1 or 2 hetero atoms selected from N, O and S;
$R^1$ is each independently a hydrogen atom or an aliphatic group; and
$R^2$ is an aliphatic group,
or a pharmaceutically acceptable salt thereof, for use in the prophylaxis or treatment of Sjogren's syndrome.

[10] The compound of the above-mentioned [9], wherein R is an aliphatic group, alkoxy or haloalkoxy, or a pharmaceutically acceptable salt thereof.

[11] The compound of the above-mentioned [9], wherein the compound represented by the formula (I) is N-{4-chloro-2-[(1-oxidopyridin-4-yl)carbonyl]phenyl}-4-(propan-2-yloxy)benzenesulfonamide, or a pharmaceutically acceptable salt thereof.

[12] The compound of the above-mentioned [9], wherein the compound represented by the formula (I) is N-{4-chloro-2-[(1-oxidopyridin-4-yl)carbonyl]phenyl}-4-(tert-butyl)benzenesulfonamide, or a pharmaceutically acceptable salt thereof.

[13] Use of a compound represented by the formula (I):

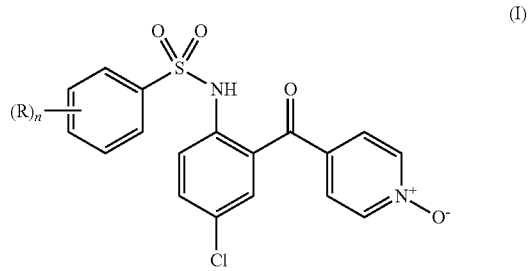

wherein n is an integer of 1-3;
R is each independently an aliphatic group, haloalkyl, aryl, arylalkyl, alkoxy, cycloalkoxy, haloalkoxy, aryloxy, arylalkoxy, alkylthio, a halogen atom, nitro, cyano, hydroxy, $NR^1CO_2R^2$, $C(O)N(R^1)_2$, $C(O)R^2$, $CO_2R^2$, $OC(O)N(R^1)_2$, $OC(O)R^2$, $N(R^1)_2$ or $NR^1C(O)R^2$; or two adjacent R groups form, together with an atom bonded thereto, a condensed, saturated, unsaturated, or partially unsaturated 5- to 7-membered ring having 0, 1 or 2 hetero atoms selected from N, O and S;
$R^1$ is each independently a hydrogen atom or an aliphatic group; and
$R^2$ is an aliphatic group,
or a pharmaceutically acceptable salt thereof, for the manufacture of a prophylactic or therapeutic agent for Sjogren's syndrome.

[14] The use of the above-mentioned [13], wherein R is an aliphatic group, alkoxy or haloalkoxy.

[15] The use of the above-mentioned [13], wherein the compound represented by the formula (I) is N-{4-chloro-2-[(1-oxidopyridin-4-yl)carbonyl]phenyl}-4-(propan-2-yloxy)benzenesulfonamide.

[16] The use of the above-mentioned [13], wherein the compound represented by the formula (I) is N-{4-chloro-2-[(1-oxidopyridin-4-yl)carbonyl]phenyl}-4-(tert-butyl)benzenesulfonamide.

Effect of the Invention

According to the present invention, a novel prophylactic or therapeutic agent and a prophylactic or therapeutic method for Sjogren's syndrome can be provided. According to the present invention, moreover, (1) glandular symptoms (dry eye, dry mouth etc.), (2) extraglandular symptoms (fatigue, low fever, polyarthritis, Raynaud's phenomenon, interstitial nephritis, renal tubular acidosis, interstitial pneumonia, lymphoproliferative disorders, drug hypersensitivity symptom, skin symptom etc.) and the like can be improved. Furthermore, according to the present invention, recurrence of Sjogren's syndrome and various symptoms of Sjogren's syndrome can be suppressed, and the present invention can also delay the progression of Sjogren's syndrome and various symptoms of Sjogren's syndrome.

Figure 1:
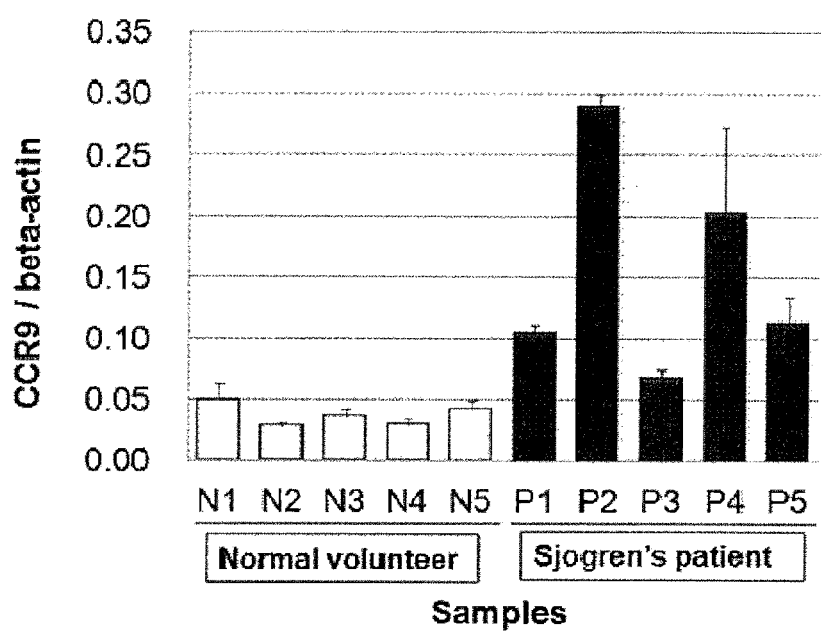
FIG. 1 shows the results of Experimental Example 1, wherein CCR9 relative expression levels (mean and standard deviation in duplicate experiment) of peripheral blood cells of patients with Sjogren's syndrome (sample name: P1-P5) and 5 healthy individuals (sample name: N1-N5) are shown.

The present invention is explained in detail in the following.

The definition of each substituent in compound (I) is shown below.

n is an integer of 1-3, and is preferably an integer of 1.

Examples of the "aliphatic group" for R include a straight chain, branched or cyclic hydrocarbon group. The hydrocarbon includes a completely saturated hydrocarbon and an unsaturated and nonaromatic hydrocarbon. The "aliphatic group" is optionally substituted.

Examples of the "hydrocarbon group" include straight chain or branched alkyl, straight chain or branched alkenyl, straight chain or branched alkynyl, cycloalkyl, cycloalkenyl, and hybrids thereof such as (cycloalkyl)alkyl, (cycloalkenyl)alkyl, (cycloalkyl)alkenyl).

Examples of the "alkyl" include $C_{1-12}$ alkyl such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl and dodecyl. Of these, $C_{1-8}$ alkyl is preferable, $C_{1-6}$ alkyl is more preferable, and tert-butyl is particularly preferable.

Examples of the "alkenyl" include $C_{2-12}$ alkenyl such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl and 1-octenyl.

Examples of the "alkynyl" include $C_{2-12}$ alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl and 1-octynyl.

Examples of the "cycloalkyl" include $C_{3-12}$ cycloalkyl such as cyclopropyl, cyclobutyl, cyclopentyl, cyclohexyl, cycloheptyl and cyclooctyl.

Examples of the "cycloalkenyl" include $C_{3-12}$ cycloalkenyl such as 2-cyclopenten-1-yl, 3-cyclopenten-1-yl, 2-cyclohexen-1-yl and 3-cyclohexen-1-yl.

Examples of the (cycloalkyl)alkyl include $C_{3-12}$ cycloalkyl $C_{1-12}$ alkyl. Examples of the "cycloalkyl" moiety and "alkyl" moiety include those similar to the above-mentioned "cycloalkyl" and "alkyl." Examples of the (cycloalkenyl)alkyl include $C_{3-12}$ cycloalkenyl $C_{1-12}$ alkyl. Examples of the "cycloalkenyl" moiety and "alkyl" moiety include those similar to the above-mentioned "cycloalkenyl" and "alkyl." Examples of the (cycloalkyl)alkenyl include $C_{3-12}$ cycloalkyl $C_{2-12}$ alkenyl. Examples of the "cycloalkyl" moiety and "alkenyl" moiety include those similar to the above-mentioned "cycloalkyl" and "alkenyl."

The "haloalkyl" for R is alkyl substituted by one or more halogen atoms, and examples of the "alkyl" include those similar to the above-mentioned "alkyl" such as $C_{1-12}$ alkyl. The "halogen atom" means a fluorine atom, a chlorine atom, a bromine atom or an iodine atom.

Examples of the "aryl" for R include $C_{6-14}$ aryl, a monocyclic or condensed polycyclic aromatic ring group such as phenyl, naphthyl, anthracenyl; and an aromatic ring condensed with one or more nonaromatic rings such as indanyl, 1,2,3,4-tetrahydronaphthyl. The "aryl" is optionally substituted. Examples of the "aryl" moiety and "alkyl" moiety of the is "arylalkyl" for R include those similar to the above-mentioned "aryl" and "alkyl." Examples of the "arylalkyl" include $C_{6-14}$ aryl $C_{1-12}$ alkyl such as benzyl and phenethyl.

Examples of the "alkyl" moiety of the "alkoxy" for R include those similar to the above-mentioned "alkyl." Examples of the "alkoxy" include $C_{1-12}$ alkoxy such as methoxy, ethoxy, propoxy, isopropoxy, butoxy, isobutoxy, sec-butoxy, tert-butoxy, pentyloxy, isopentyloxy, neopentyloxy, 1-ethylpropoxy, hexyloxy, isohexyloxy, 1,1-dimethylbutoxy, 2,2-dimethylbutoxy, 3,3-dimethylbutoxy, 2-ethylbutoxy, heptyloxy, octyloxy, nonyloxy, decyloxy, undecyloxy and dodecyloxy. Of these, $C_{1-8}$ alkoxy is preferable, $C_{1-6}$ alkoxy is more preferable, and isopropoxy is particularly preferable.

Examples of the "cycloalkyl" of the "cycloalkoxy" for R include those similar to the above-mentioned "cycloalkyl." Examples of the "cycloalkoxy" include $C_{3-12}$ cycloalkoxy such as cyclopropoxy and cyclobutoxy.

The "haloalkoxy" for R is alkoxy substituted by one or more (preferably 1-3) halogen atoms and examples of the "alkoxy" include those similar to the above-mentioned "alkoxy" such as $C_{1-12}$ alkoxy. The "halogen atom" is a fluorine atom, a chlorine atom, a bromine atom or an iodine atom. Preferable examples of said "haloalkoxy" include $C_{1-12}$ alkoxy substituted by 1 to 3 halogen atoms such as chloromethoxy, fluoromethoxy, difluoromethoxy, trifluoromethoxy, 2-bromoethoxy, 2,2,2-trifluoroethoxy, pentafluoroethoxy, 1,3-difluoroisopropoxy, 4,4,4-trifluorobutoxy and the like.

Examples of the "aryl" moiety of the "aryloxy" for R include those similar to the above-mentioned "aryl." Examples of the "aryloxy" include $C_{6-14}$ aryloxy such as phenoxy.

Examples of the "aryl" moiety and "alkoxy" moiety of the "arylalkoxy" for R include those similar to the above-mentioned "aryl" and "alkoxy." Examples of the "arylalkoxy" include $C_{6-14}$ aryl $C_{1-12}$ alkoxy such as phenylmethoxy.

Examples of the "alkyl" moiety of the "alkylthio" for R include those similar to the above-mentioned "alkyl" such as $C_{1-12}$ alkyl.

The "halogen atom" for R is a fluorine atom, a chlorine atom, a bromine atom or an iodine atom.

Examples of the "aliphatic group" for $R^1$ or $R^2$ include those similar to the above-mentioned "aliphatic group".

Examples of the "condensed, saturated, unsaturated, or partially unsaturated 5- to 7-membered ring having 0, 1 or 2 hetero atoms selected from N, O and S, which is formed by two adjacent R groups, together with an atom bonded thereto" include cyclopentene, dihydrofuran, furan, thiophene, pyrazole, pyridine, tetrahydropyridine and azepine.

In the present invention, R is preferably an aliphatic group, alkoxy or haloalkoxy, more preferably an aliphatic group (particularly tert-butyl) or alkoxy (particularly isopropoxy).

In the present invention, a compound wherein n is 1 and R is at the para-position relative to a sulfonamide group is preferable.

Compound (I) of the present invention is preferably N-{4-chloro-2-[(1-oxidopyridin-4-yl)carbonyl]phenyl}-4-(propan-2-yloxy)benzenesulfonamide:

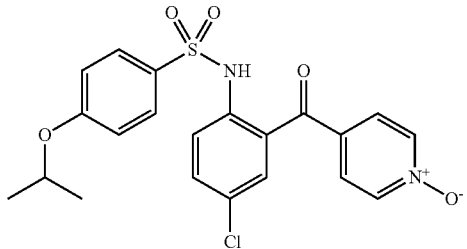 [SMILES: CC(C)Oc1ccc(S(=O)(=O)Nc2ccc(Cl)cc2C(=O)c2cc[n+]([O-])cc2)cc1]

or N-{4-chloro-2-[(1-oxidopyridin-4-yl)carbonyl]phenyl}-4-(tert-butyl)benzenesulfonamide:

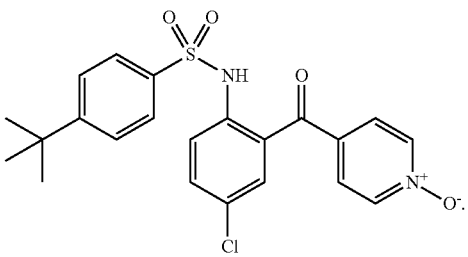

The above-mentioned "aliphatic group" may have one or more substituents. Examples of the substituent include amino, alkylamino (e.g., methylamino, ethylamino etc.), dialkylamino (e.g., dimethylamino etc.), aminocarbonyl, a halogen atom (e.g., fluorine atom, chlorine atom, bromine atom, iodine atom), alkyl (e.g., $C_{1-6}$ alkyl such as methyl, ethyl, etc., and the like), alkylaminocarbonyl (e.g., $C_{1-6}$ alkylamino-carbonyl such as methylaminocarbonyl etc., and the like), dialkylaminocarbonyl (e.g., di-$C_{1-6}$ alkyl-aminocarbonyl such as dimethylaminocarbonyl, etc. and the like), alkylaminocarbonyloxy (e.g., $C_{1-6}$ alkylamino-carbonyloxy such as methylaminocarbonyloxy etc., and the like), dialkylaminocarbonyloxy (e.g., di-$C_{1-6}$ alkyl-aminocarbonyloxy such as dimethylaminocarbonyloxy etc., and the like), alkoxy (e.g., $C_{1-6}$ alkoxy such as methoxy, ethoxy etc., and the like), thioalkyl (e.g., thiomethyl etc.), nitro, cyano, carboxy, alkoxycarbonyl (e.g., $C_{1-6}$ alkoxy-carbonyl such as methoxycarbonyl, ethoxycarbonyl etc., and the like), alkylcarbonyl (e.g., $C_{1-6}$ alkyl-carbonyl such as acetyl etc., and the like), hydroxy, haloalkoxy (e.g., halo-$C_{1-6}$ alkoxy such as chloromethoxy etc., and the like), haloalkyl (e.g., halo-$C_{1-6}$ alkyl such as chloromethyl etc., and the like) and the like.

The above-mentioned "aryl" may have one or more substituents. Examples of the substituent include aliphatic group (e.g., those similar to the "aliphatic group" for the aforementioned R), aryl (e.g., $C_{6-14}$ aryl such as phenyl etc., and the like), haloalkoxy (e.g., halo-$C_{1-6}$ alkoxy such as chloromethoxy etc., and the like), heteroaryl (e.g., 5- or 6-membered monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc., and the like), a halogen atom (e.g., fluorine atom, chlorine atom, bromine atom, iodine atom), hydroxy, $OR^4$, $COR^4$, $COOR^4$, $NHCOR^4$, $OCOR^4$, benzyl, haloalkyl (e.g., halo-$C_{1-6}$ alkyl such as chloromethyl etc., and the like), cyano, nitro, S(O), $S(O)_2$, $SO_3^-$, SH, $SR^4$, $NH_2$, $NHR^4$, $NR^4R^5$, $NR^6S(O)_2$—$R^7$ and COOH, wherein $R^4$ and $R^5$ are each independently an aliphatic group (e.g., those similar to the aforementioned "aliphatic group" for R), cycloalkyl (e.g., $C_{3-6}$ cycloalkyl such as cyclopropyl, cyclobutyl, cyclopentyl, cyclohexyl etc., and the like), aryl (e.g., $C_{6-14}$ aryl such as phenyl etc., and the like), arylalkyl (e.g., $C_{6-14}$ aryl $C_{1-12}$ alkyl such as benzyl etc., and the like) and the like. $R^6$ and $R^7$ are each independently an aliphatic group (e.g., those similar to the aforementioned "aliphatic group" for R), cycloalkyl (e.g., $C_{3-6}$ cycloalkyl such as cyclopropyl, cyclobutyl, cyclopentyl, cyclohexyl etc., and the like), aryl (e.g., $C_{6-14}$ aryl such as phenyl etc., and the like), arylalkyl (e.g., $C_{6-14}$ aryl $C_{1-12}$ alkyl such as benzyl etc., and the like) and the like.

Examples of the pharmaceutically acceptable salt of compound (I) include salt with inorganic base, salt with organic base, salt with inorganic acid, salt with organic acid, salt with basic or acidic amino acid and the like.

Examples of the salt with inorganic base include alkali metal salts such as sodium salt, potassium salt and the like; alkaline earth metal salts such as calcium salt, magnesium salt and the like; aluminum salt, ammonium salt and the like.

Examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Examples of the salt with inorganic acid include salts with hydrochloric acid, hydrobromic acid, nitric acid, sulfuric acid, phosphoric acid and the like.

Examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, benzoic acid and the like.

Examples of the salt with basic amino acid include salts with arginine, lysine, ornithine and the like.

Examples of the salt with acidic amino acid include aspartic acid, glutamic acid and the like.

Compound (I) or a pharmaceutically acceptable salt thereof may be a solvate (e.g., hydrate) or a non-solvate (e.g., non-hydrate), and these are encompassed in compound (I) or a pharmaceutically acceptable salt thereof.

Compound (I) or a pharmaceutically acceptable salt thereof may be a crystal, and the crystal form of the crystal may be single or plural. The crystal can be produced by a known crystallization method.

Compound (I) or pharmaceutically acceptable salt thereof has low toxicity (e.g., acute toxicity, chronic toxicity, genetic toxicity, reproductive toxicity, cardiotoxicity, drug interaction, carcinogenicity) at an efficacy dose, can be used as an agent for the prophylaxis or treatment of Sjogren's syndrome in a mammal (e.g., human, mouse, rat, rabbit, dog, cat, bovine, horse, swine, monkey) directly or in the form of a pharmaceutical composition by admixing with a pharmacologically acceptable carrier and the like. Sjogren's syndrome includes primary and secondary Sjogren's syndrome.

Examples of the symptoms of primary Sjogren's syndrome include
(1) glandular symptoms (dry eye, dry mouth etc.),
(2) extraglandular symptoms (fatigue, low fever, polyarthritis, Raynaud's phenomenon, interstitial nephritis, renal tubular acidosis, interstitial pneumonia, lymphoproliferative disorders, drug hypersensitivity symptom, skin symptoms (cheilitis, angular cheilitis, glossitis, blepharitis, xeroderma, recurrent erythema annulare centrifugum, erythema nodosum, erythema palmare, chiblain rash, livedo reticularis, photosensitivity, hypergammaglobulinemia purpura, drug eruption, contact dermatitis (eye drop dermatitis etc.), melanosis faciej feminine rash, lichen planus, sarcoidosis, skin amyloidocis, diffuse hair loss etc.) and the like). Compound (I) or a pharmaceutically acceptable salt thereof can be used for the improvement of the above-mentioned symptoms.

Examples of the symptoms of secondary Sjogren's syndrome include rheumatoid arthritis, systemic lupus erythematosus, mixed connective-tissue disease, scleroderma, polymyositis/dermatomyositis and the like.

When compound (I) or a pharmaceutically acceptable salt thereof is used for the improvement of glandular symptoms (dry eye, dry mouth etc.), it can be used in combination with, for example, humidifier, artificial lacrimal fluid, eye drop and the like.

Compound (I) or a pharmaceutically acceptable salt thereof can be used in combination with, for example, non-steroidal anti-inflammatory drugs (e.g., aspirin, naproxen, ibuprofen, indomethacin, tolmetin etc.), corticosteroids (e.g., prednisolone, methylprednisolone, hydrocortisone, dexamethasone etc.), muscarine receptor agonists (e.g., pilocarpine, cevimeline etc.), mucolytic agents (e.g., bromhexine, N-acetylcysteine etc.), immune suppressants (e.g., cyclosporine, azathiopurine, methotrexate, mycophenolic acid, leflunomide, cyclophosphamide, chlorambucil, tacrolimus etc.), anti-malaria agents (e.g., hydroxychloroquine etc.), immunoglobulin for intravenous injection, biologics (e.g., anti-CD20 antibody (e.g., rituximab etc.), anti-BAFF antibody (e.g., belimumab etc.), anti-CD22 antibody (e.g., epratuzumab etc.), anti-IL-6 receptor antibody (e.g., tocilizumab etc.), anti-TNF-$\alpha$ antibody (e.g., infliximab, etanercept, adalimumab etc.), anti-$\alpha$-4 integrin antibody (e.g., natalizumab etc.), CTLA4-Ig (e.g., abatacept etc.), TACI-Ig (e.g., atacicept etc.)) and the like, according to various symptoms of Sjogren's syndrome, for patients with complications.

Examples of the pharmacologically acceptable carrier include various organic or inorganic carrier substances conventionally used as preparation materials, which are added as excipient, lubricant, binder, disintegrant for solid preparations; solvent, solubilizing agent, suspending agent, isotonicity agent, buffer, soothing agent for liquid preparation. Where necessary, preparation additives such as preservative, antioxidant, colorant, sweetening agent and the like can also be used.

Examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate, magnesium alumino metasilicate and the like.

Examples of the lubricant include magnesium stearate, calcium stearate, talc, colloidal silica and the like.

Examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose, polyvinylpyrrolidone and the like.

Examples of the disintegrant include lactose, sucrose, starch, carboxymethylcellulose, calcium carboxymethylcellulose, croscarmellose sodium, sodium carboxymethyl starch, light anhydrous silicic acid, low-substituted hydroxypropylcellulose and the like.

Examples of the solvent include water for injection, physiological brine, Ringer's solution, alcohol, propylene glycol, polyethylene glycol, sesame oil, corn oil, olive oil, cottonseed oil and the like.

Examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Examples of the suspending agent include surfactants such as stearyltriethanolamine, sodium lauryl sulfate, lauryl aminopropionic acid, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydrcxymethylcellulose, hydroxyethylcellulocse, hydroxypropylcellulose and the like; polysorbates, polyoxyethylene hydrogenated castor oil and the like.

Examples of the isotonic agent include sodium chloride, glycerol, D-mannitol, D-sorbitol, glucose and the like.

Examples of the buffer include buffers such as phosphate, acetate, carbonate, citrate and the like.

Examples of the soothing agent include benzyl alcohol and the like.

Examples of the preservative include paraoxybenzoates, chlorobutanol, benzyl alcohol, phenethyl alcohol, dehydroacetic acid, sorbic acid and the like.

Examples of the antioxidant include sulfite, ascorbate and the like.

Examples of the colorant include aqueous food tar colors (e.g., food colors such as Food Red Nos. 2 and 3, Food Yellow Nos. 4 and 5, Food Blue Nos. 1 and 2 and the like), water insoluble lake dyes (e.g., aluminum salt of the aforementioned aqueous food tar color), natural dyes (e.g., $\beta$-carotene, chlorophyll, ferric oxide red) and the like.

Examples of the sweetening agent include saccharin sodium, dipotassium glycyrrhizinate, aspartame, stevia and the like.

The solid preparation may be coated by a known method. As the coating agent, hydroxypropylmethylcellulose (e.g., hypromellose 2910), ethylcellulose, hydroxypropylcellulose, polyethylene glycol (e.g., macrogol 6000), Tween 80, and dye such as titanium oxide, ferric oxide red (e.g., red ferric oxide, yellow ferric oxide) and the like are used.

Examples of the dosage form of the aforementioned pharmaceutical composition include oral preparations such as tablet (including sugar-coated tablet, film-coated tablet, sublingual tablet, orally disintegrating tablet), capsule (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, nasal preparations, pulmonary preparation (inhalant), eye drop and the like. Each of these can be safely administered orally or parenterally (e.g., topical, rectal, intravenous administration). These preparations may be release control preparations such as immediate-release preparations or sustained-release preparations and the like (e.g., sustained-release microcapsule).

The pharmaceutical composition can be produced by a method conventionally used in the technical field of pharmaceutical preparation, for example, the method described in the Japanese Pharmacopoeia and the like.

While the content of compound (I) or pharmaceutically acceptable salt thereof in the pharmaceutical composition varies depending on the dosage form, dose and the like, it is, for example, about 0.01-about 99 wt %, preferably about 0.1-about 99 wt %.

While the dose of compound (I) or pharmaceutically acceptable salt thereof varies depending on the subject of administration, administration route, severity and the like, for example, for oral administration to an adult Sjogren's syndrome patient, it is generally about 0.01-about 100 mg/kg body weight, preferably about 0.5-about 50 mg/kg body weight for a single dose, which is desirably administered once to 3 times a day.

Of compound (I) and a pharmaceutically acceptable salt thereof, when compound A or a pharmaceutically acceptable salt thereof is orally administered of to an adult Sjogren's syndrome patient, a single dose is generally about 0.01-about 100 mg/kg body weight, preferably about 0.05-about 50 mg/kg body weight, which is desirably administered once to 3 times a day. For oral administration of compound B or a pharmaceutically acceptable salt thereof to an adult Sjogren's syndrome patient, a single dose is generally about 0.01-about 50 mg/kg body weight, preferably about 0.05-about 25 mg/kg body weight, which is desirably administered once to 3 times a day.

Compound (I) can be produced by a known method, for example, the method described in WO2003/099773 or WO2004/046092, or a method analogous thereto. Compound A can be produced according to Example 119 of WO2003/099773, and compound B can be produced according to Example 32 of WO2004/046092.

In addition, compound (I) can also be produced according to the following method.

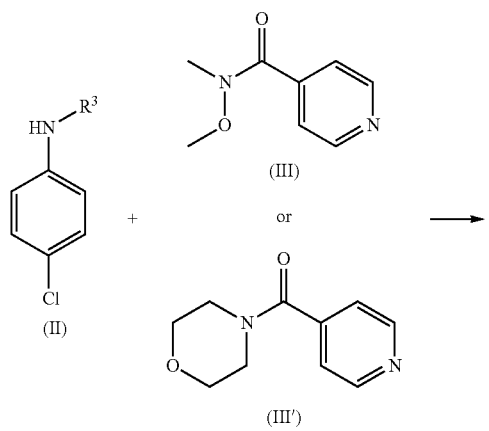

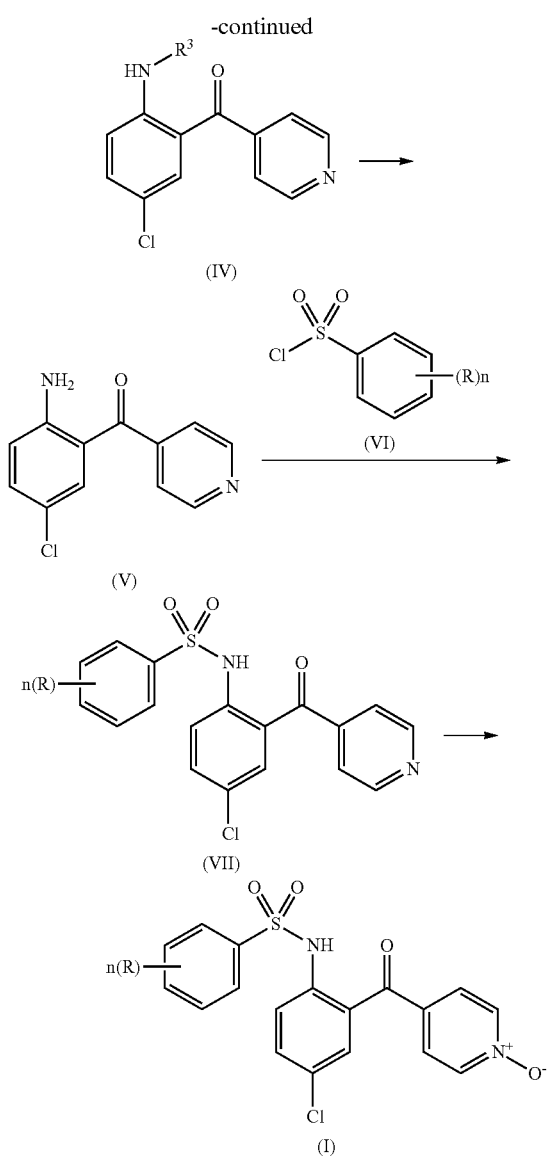

In each formula, $R^3$ is an amino-protecting group, and R and n are as defined above.

Compound (II) can be obtained by protecting the amino group of 4-chloroaniline with a protecting group (e.g., pivaloyl group). The reaction can be performed by reacting, for example, 4-chloroaniline with pivaloyl chloride in a solvent (e.g., ethyl acetate, water) in the presence of a base (e.g., sodium hydrogen carbonate) at a reaction temperature of about −20-about 100° C. for about 0.1-about 50 hr. The amount of pivaloyl chloride to be used is generally about 0.3-about 5 mol per 1 mol of 4-chloroaniline. The amount of the base to be used is generally about 0.3-about 5 mol per 1 mol of 4-chloroaniline.

While compound (II) can be isolated and purified from the reaction mixture by a known means, for example, extraction, concentration, neutralization, filtration, crystallization, recrystallization, column chromatography, thin layer chromatography and the like, the reaction mixture may be directly used without isolation as a starting material for the next step.

Compound (III) can be produced by a known method, for example, the method described in WO2003/099773, or a method analogous thereto.

Compound (III') can be produced by reacting isonicotinic acid with a halogenating agent such as thionyl chloride and the like in a solvent (e.g., dimethylformamide, tetrahydrofuran) at a reaction temperature of about −20-about 100° C. for about 0.1-about 50 hr, and reacting the obtained compound with morpholine in a solvent (e.g., dimethylformamide, tetrahydrofuran) in the presence of a base (e.g., sodium carbonate) at a reaction temperature of about −20-about 100° C. for about 0.1-about 50 hr. The amount of the halogenating agent to be used such as thionyl chloride and the like is generally about 0.3-about 5 mol per 1 mol of isonicotinic acid. The amount of morpholine to be used is generally about 0.3-about 5 mol per 1 mol of isonicotinic acid. The amount of the base to be used is generally about 0.3-about 5 mol per 1 mol of isonicotinic acid.

While compound (III) and compound (III') can be isolated and purified from the reaction mixture by the above-mentioned known means, the reaction mixture may be directly used without isolation as a starting material for the next step.

Compound (IV) can be obtained by treating compound (II) and compound (III) or compound (III') with alkyllithium (e.g., n-butyllithium, sec-butyllithium, tert-butyllithium).

Compound (IV) can be produced by reacting compound (II) with alkyllithium in a solvent (e.g., tetrahydrofuran) at a reaction temperature of about −78-about 50° C. for about 0.1-about 50 hr, and reacting the obtained compound with compound (III) or compound (III') in a solvent (e.g., tetrahydrofuran) at a reaction temperature of about −20-about 50° C. for about 0.1-about 50 hr. The amount of alkyllithium to be used is generally about 0.3-about 5 mol per 1 mol of compound (II). The amount of compound (III) or compound (III') to be used is generally about 0.3-about 5 mol per 1 mol of compound (II).

While compound (IV) can be isolated and purified from the reaction mixture by the above-mentioned known means, the reaction mixture may be directly used without isolation as a starting material for the next step.

Compound (V) can be produced by reacting, for example, compound (IV) in a solvent (e.g., methanol, tetrahydrofuran) in the presence of a base (e.g., potassium hydroxide) at a reaction temperature of about −20-about 100° C. for about 0.1-about 50 hr, and removing the amino-protecting group. The amount of the base to be used is generally about 0.3-about 5 mol per 1 mol of compound (IV).

While compound (V) can be isolated and purified from the reaction mixture by the above-mentioned known means, the reaction mixture may be directly used without isolation as a starting material for the next step.

Compound (VII) can be produced by reacting compound (V) with compound (VI) in a solvent (e.g., pyridine) in the presence of a base (e.g., pyridine, sodium hydride, sodium bis(trimethylsilyl)amide) at a reaction temperature of about 0-about 120° C. for about 0.1-about 50 hr. The amount of compound (VI) to be used is generally about 0.3-about 5 mol per 1 mol of compound (V). The amount of the base to be used is generally about 0.3-about 5 mol per 1 mol of compound (V).

While compound (VII) can be isolated and purified from the reaction mixture by the above-mentioned known means, the reaction mixture may be directly used without isolation as a starting material for the next step.

Compound (I) can be produced by reacting compound (VII) with hydrogen peroxide and acetic acid at about −20-about 100° C. for about 0.1-about 50 hr. The amount of hydrogen peroxide to be used is generally about 0.1-about 5 mol per 1 mol of compound (VII). The amount of acetic acid to be used is generally about 1-about 100 mL per 1 g of compound (VII). Compound (I) can be isolated and purified from the reaction mixture by the above-mentioned known means.

A pharmaceutically acceptable salt of compound (I) can be produced by a known method.

EXAMPLES

The present invention is explained in detail in the following by referring to Examples, Formulation Examples, and Experimental Examples, which are not to be construed as limitative. In the Examples, Formulation Examples and Experimental Examples, compound A is N-{4-chloro-2-[(1-oxidopyridin-4-yl)carbonyl]phenyl}-4-(propan-2-yloxy)benzenesulfonamide, and compound B is N-{4-chloro-2-[(1-oxidopyridin-4-yl)carbonyl]phenyl}-4-(tert-butyl)benzenesulfonamide (aka: 4-tert-butyl-N-(4-chloro-2-(1-oxidoisonicotinoyl)phenyl)benzenesulfonamide).

In the following Examples, the "room temperature" is generally about 10° C. to about 35° C. The ratio shown for mixed solvent is a volume mixing ratio, unless otherwise specified. % is wt %, unless otherwise specified.

In silica gel column chromatography, NH means use of aminopropylsilane-bound silica gel, Diol means use of 3-(2,3-dihydroxypropoxy)propylsilane-bound silica gel, and DiNH means use of N-(2-aminoethyl)-3-aminopropylsilane-bound silica gel. In HPLC (high performance liquid chromatography), C18 means use of octadecyl-bound silica gel. The ratio of the elution solvents is a volume mixing ratio, unless otherwise specified.

In the following Examples, the following abbreviations are used.

mp: melting point

MS: mass spectrum

M: mole concentration $CDCl_3$: deuterated chloroform $DMSO\text{-}d_6$: deuterated dimethyl sulfoxide $^1H$ NMR: proton nuclear magnetic resonance LC/MS: liquid chromatography mass spectrometer ESI: electrospray ionization APCI: atmospheric pressure chemical ionization DME: 1,2-dimethoxyethane DMA: N,N-dimethylacetamide HATU: 2-(7-azabenzotriazol-1-yl)-1,1,3,3-tetramethyluronium hexafluorophosphate HOBt: 1-hydroxybenzotriazole $^1H$ NMR was measured by Fourier-transform type NMR. Peaks with very mild protons such as hydroxyl group, amino group and the like are not described.

MS was measured by LC/MS. As the ionization method, ESI method or APCI method was used. The data indicates those found. Generally, a molecular ion peak ($[M+H]^+$, $[M-H]^-$ and the like) is observed. For example, in the case of a compound having a tert-butoxycarbonyl group, a peak after elimination of a tert-butoxycarbonyl group or tert-butyl group may be observed as a fragment ion, and in the case of a compound having a hydroxyl group, a peak after elimination of $H_2O$ may be observed as a fragment ion. In the case of a salt, a molecular ion peak or fragment ion peak of free form is generally observed.

Elemental analysis value (Anal.) describes calculated values (Calcd) and those actually found (Found).

Example 1

Compound A was produced by the following steps 1-6.

Step 1: Synthesis of
N-(4-chlorophenyl)-2,2-dimethyl-propionamide

Step 1

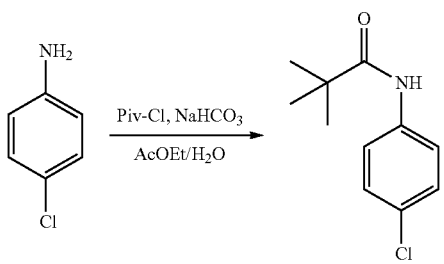

4-Chloroaniline (100 g) was dissolved in ethyl acetate (1500 mL), water (500 mL) and sodium hydrogen carbonate (79 g) were added, pivaloylchloride (99 g) was added at 5-15° C., and the mixture was stirred at 20-30° C. for about 2 hr. The mixture was partitioned, and the organic layer was washed twice with water (750 mL) and concentrated to about 500 mL under reduced pressure. Ethylcyclohexane (750 mL) was added, and the mixture was concentrated to about 500 mL. The concentrated residue was cooled to 0-5° C., and the mixture was stirred while aging the crystals at the same temperature for 1 hr. The precipitated crystals were collected by filtration, washed with cold ethylcyclohexane (200 mL), and dried under reduced pressure to give the title compound as crystals. Standard yield: 95±10%

Step 2: Synthesis of
morpholin-4-yl(pyridin-4-yl)methanone

Step 2

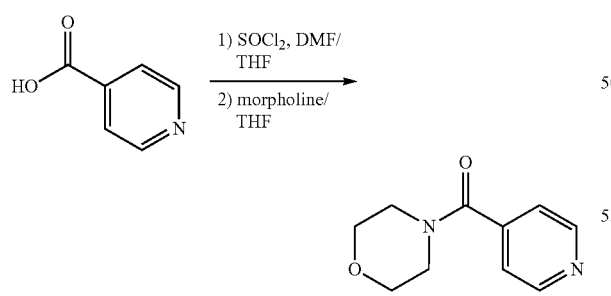

Under a nitrogen atmosphere, isonicotinic acid (10 g) and dimethylformamide (60 mg) were added to tetrahydrofuran (150 mL) at 20-25° C., and the mixture was stirred. The mixture was heated to 55-65° C., thionyl chloride (12 g) was added dropwise at 55-65° C., and the mixture was stirred for about 3 hr. After cooling to 5-15° C., morpholine (16 g) was added dropwise at 25° C. or below, and the mixture was stirred at 20-30° C. for about 3 hr. The reaction mixture was cooled to 5° C. or below, adjusted to pH 6.5-7.0 with 20% aqueous sodium carbonate solution, and the mixture was stirred for 1 hr or longer. The precipitate was collected by filtration, and the insoluble material was washed with tetrahydrofuran (30 mL). The filtrate and the washing were combined, and the organic layer was separated. To the aqueous layer was added ethyl acetate (50 mL), the mixture was extracted 5-7 times, and the organic layer was concentrated to about 30 mL under reduced pressure. To the concentrated solution was added cyclopentylmethylether (20 mL), and the mixture was concentrated to about 30 mL under reduced pressure. This concentration operation was repeated three times, cyclopentyl methyl ether (10 mL) was added, and the mixture was concentrated to 25 mL under reduced pressure. Tetrahydrofuran (15 mL) was added to give a solution containing the title compound, which solution was used for the next step. Standard yield: 90±10% morpholin-4-yl(pyridin-4-yl)methanone: $^1$H NMR (Bruker 500 MHz CDCl$_3$, shift corresponding to the peak of the solvent at δ7.27 ppm) 53.38 (s, 2H) 3.63 (s, 2H) 3.79 (s, 2H) 7.28-7.30 (d, 2H) 8.71-8.72 (d, 2H)

Step 3: Synthesis of
(2-amino-5-chlorophenyl)pyridin-4-ylmethanone

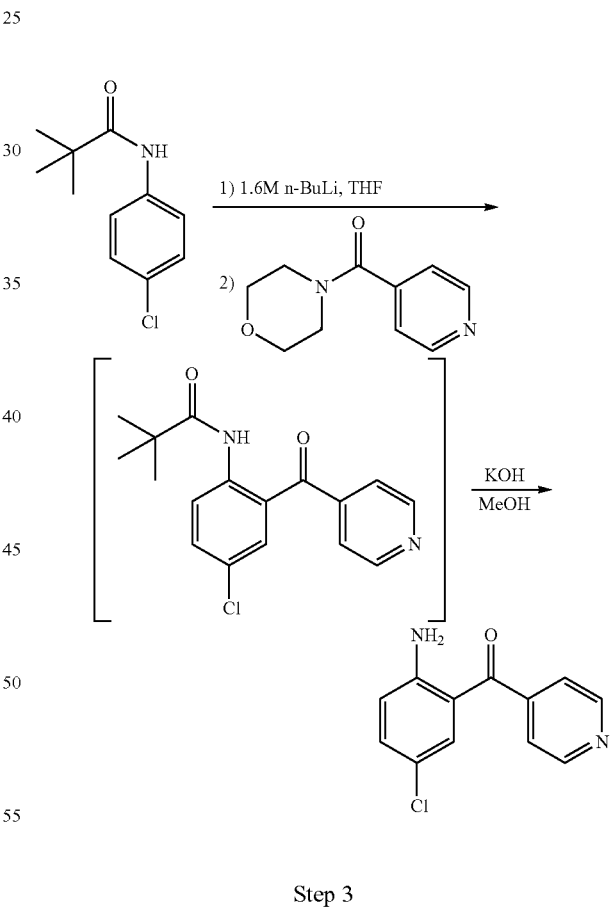

Step 3

Under a nitrogen atmosphere, N-(4-chlorophenyl)-2,2-dimethylpropionamide (6.5 g) and tetrahydrofuran (52 mL) were added, and the mixture was cooled to −30° C. 1.6M n-Butyllithium (n-BuLi) in hexane (48.1 mL) was added dropwise at −30 to −20° C., and the mixture was stirred for 2 hr and warmed to room temperature. A solution (20 mL) of morpholin-4-yl(pyridin-4-yl)methanone obtained in step 2 was added dropwise at 15-25° C., and tetrahydrofuran (5 mL)

was added. After stirring at around room temperature for 4 hr, 15% aqueous ammonium chloride solution (33 mL) was added at 25° C. or below, and the organic layer was separated. To the organic layer was added 15% aqueous ammonium chloride solution (33 mL), and the mixture was partitioned. To the organic layer was added 10% brine (33 mL), and the mixture was partitioned. The organic layer was concentrated to about 20 mL under reduced pressure, and methanol (39 ml) was added. A solution of potassium hydroxide (8.62 g) in water (17 mL) was added at 20° C. or below. After stirring at 55-65° C. for 4 hr, the mixture was cooled to 5° C. or below, and the mixture was stirred for 1 hr. The crystals were collected by filtration, washed with a mixed solution of methanol (20 mL)/tetrahydrofuran (3.3 mL) cooled to 5° C. or below, and dried under reduced pressure to give the title compound as crystals. Standard yield: 65±10%

Step 4: Synthesis of N-[4-chloro-2-(pyridine-4-carbonyl)phenyl]-4-isopropoxybenzenesulfonamide Step 4

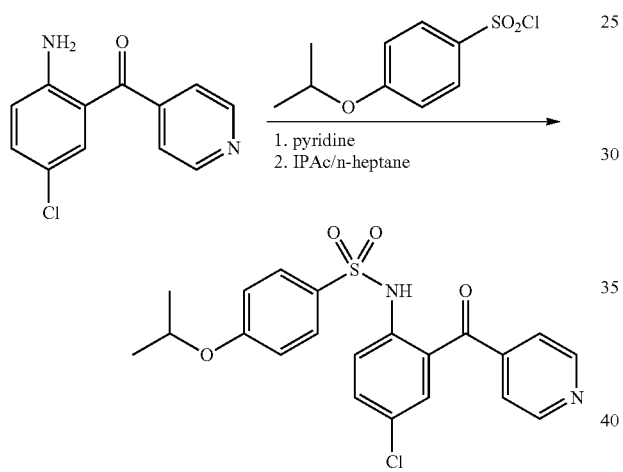

(2-Amino-5-chlorophenyl)pyridin-4-ylmethanone (5 g) was added to pyridine (12.5 mL) at 70-80° C., and the mixture was stirred. A solution of 4-isopropoxybenzenesulfonyl chloride (5.30 g) in pyridine (10 mL) was added dropwise at 70-80° C. over 30 min, the apparatus was rinsed with pyridine (3.5 mL) and the mixture was allowed to react for about 5 hr. The mixture was cooled to 20-30° C., added to isopropyl acetate (40 mL) and the apparatus was rinsed with isopropyl acetate (20.5 mL). 2M Hydrochloric acid (68 mL) was added, and the mixture was stirred and partitioned. The organic layer was adjusted with 2M hydrochloric acid to pH3, stirred and partitioned. To the organic layer was added water (25 mL), stirred and partitioned. The organic layer was concentrated at an outer temperature of about 50° C. to about 26 mL under reduced pressure, cooled to 20-30° C. Seed crystals (5 mg) were added at about 30° C., and after confirmation of crystal precipitation, the mixture was stirred at 20-30° C. for 1 hr. n-Heptane (50 mL) was added dropwise over about 1 hr at an inside temperature of 20-30° C., and the mixture was stirred at 10° C. or below for 2.5 hr, and the crystals were collected by filtration, and washed twice with n-heptane (10 mL). The crystals were dried under reduced pressure, isopropyl acetate (45 mL) was added, and the mixture was heated to 45-50° C., dissolved and stirred for about 15 min. The reaction mixture was cooled, seed crystals (0.5 g) were added at about 25-30° C., and after confirmation of crystal precipitation, the mixture was stirred at 20-30° C. for 1 hr or longer. n-Heptane (135 mL) was added dropwise over about 1 hr at 20-30° C., and the mixture was stirred for 1.5 hr or longer. After stirring at 0-10° C. for 1 hr or longer, the crystals were collected by filtration, and washed twice with n-heptane (30 mL). The crystals were dried under reduced pressure to give the title compound. Standard yield: 85±15%

Steps 5 and 6: Synthesis of Compound A

Step 5

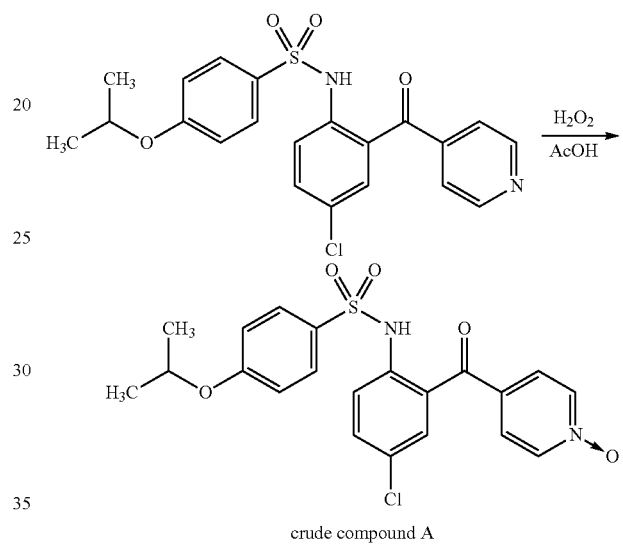

Step 6

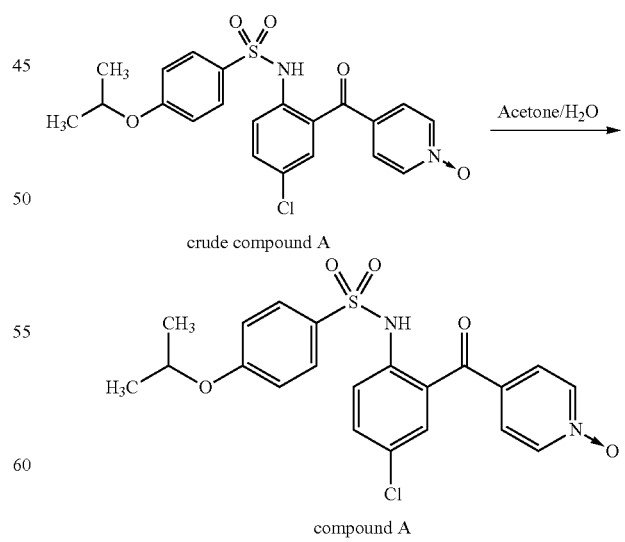

N-[4-chloro-2-(pyridine-4-carbonyl)phenyl]-4-isopropoxybenzenesulfonamide (35 g) was added to acetic acid (AcOH) (15 mL), and the mixture was heated to 50-60° C.

35% Hydrogen peroxide water (17.4 g) was added dropwise at 50-60° C., and the mixture was stirred for 8 hr or longer. Ethanol (158 mL) was added at 50° C. or below, and 0.7M aqueous sodium sulfite solution (158 mL) was further added dropwise at 40° C. or below. The mixture was cooled to 20-30° C., and stirred for 2 hr or longer. The crystals were collected by filtration, washed with an ethanol/water (35 mL/35 mL) mixture. The obtained crystals were suspended in water (105 mL), and the suspension was stirred at 30° C. or below for 30 min or longer. The crystals were separated and washed with water (70 mL). The crystals were dried under reduced pressure at 50-60° C. to give a crude compound A. Standard yield: 85±10%

To the obtained crude compound A were added acetone (123 mL) and water (14 mL), and the mixture was dissolved by heating at 55-65° C. Water (62 mL) was added dropwise, and the mixture was stirred at 55-65° C. for about 1 hr, cooled to 20-30° C. and the mixture was stirred for about 3 hr. The crystals were collected by filtration, washed with a mixture of acetone/water (12 mL/8 mL) and dried under reduced pressure at 45-55° C. to give compound A. Standard yield: 83±10%

Example 2

Compound B and a sodium salt thereof (sodium [(4-tert-butylphenyl)sulfonyl][4-chloro-2-(1-oxidoisonicotinoyl)phenyl]azanide) were produced by the following step.

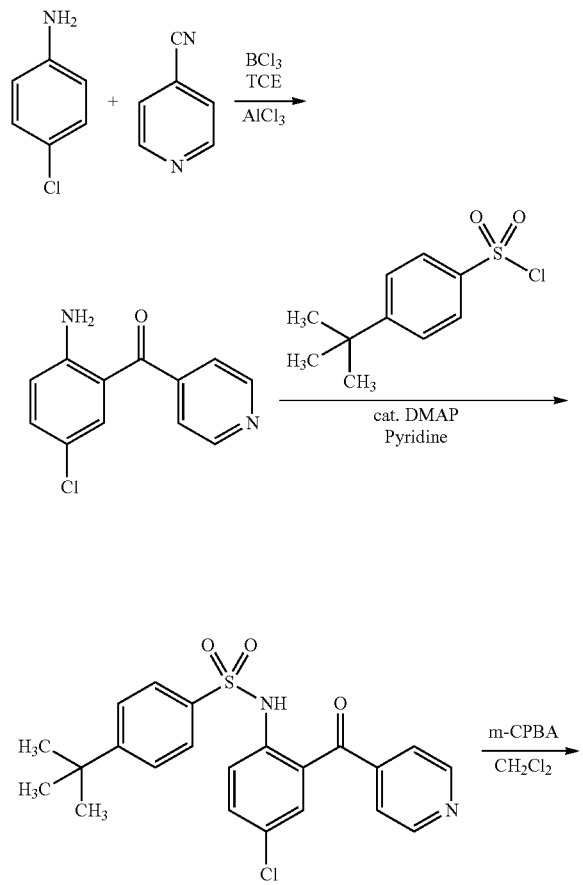

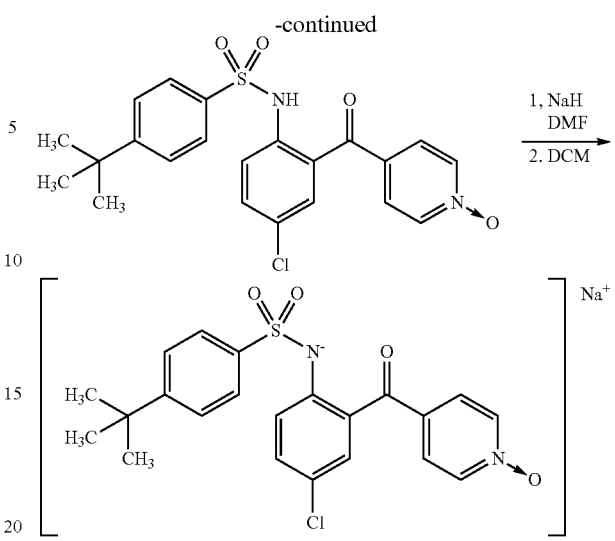

Synthesis of (2-amino-5-chlorophenyl)(pyridin-4-yl)methanone

A solution of p-chloroaniline (120 g) in trichloroethylene (1800 mL) was added to boron trichloride (1450 mL, 1.0M dichloromethane solution) at 0° C. and the mixture was stirred for 10 min. 4-Cyanopyridine (120 g) and crushed aluminum chloride (181 g) were added, and the mixture was warmed to room temperature and stirred for 30 min. After removal of dichloromethane at 80° C., and the mixture was stirred at 85° C. for 14 hr. After cooling to room temperature, 3N hydrochloric acid (1800 r) was added, and the mixture was stirred at 115° C. for 1.5 hr. The mixture was cooled to room temperature, and filtered through celite. The acidic layer was separated, and washed with chloroform. The acidic layer was adjusted to pH12 at 0° C. with 6N aqueous sodium hydroxide solution (about 2200 mL). The solid was collected by filtration, and washed with water (about 20 L). To the solid was added tert-butyl methyl ether (2000 mL), and the mixture was heated under reflux for 1 hr. After cooling to room temperature, the solid was collected by filtration and dried at 60° C. to give (2-amino-5-chlorophenyl)(pyridin-4-yl)methanone (156 g, yellow solid).
$^1$H NMR (400 MHz, CDCl$_3$) δ 6.1-6.4 (2H, brs), 6.72 (1H, dd, J=2.1, 7.3 Hz), 7.2-7.35 (2H, m), 7.44 (2H, dd, J=1.6, 4.3 Hz), 8.79 (2H, dd, J=1.6, 4.4 Hz).

Synthesis of 4-tert-butyl-N-(4-chloro-2-isonicotinoylphenyl)benzenesulfonamide

A suspension of (2-amino-5-chlorophenyl) (pyridin-4-yl)methanone (156 g) in pyridine (2350 mL) was heated at 60° C. N,N-Dimethyl-4-aminopyridine (8.21 g) and 4-tert-butylbenzenesulfonyl chloride (180 g) were added, and the mixture was heated at 75° C. for 18 hr. 4-tert-Butylbenzenesulfonyl chloride (15.6 g) was further added, and the mixture was stirred for 1 hr, and this operation was repeated 6 times. The solvent was evaporated under reduced pressure, ethyl acetate was added, and the mixture was washed twice with water (500 mL), and twice with saturated aqueous sodium hydrogen carbonate solution (500 mL). The organic layer was washed twice with 2N hydrochloric acid (200 mL), once with saturated aqueous sodium hydrogen carbonate solution (500 mL), and once with saturated brine (500 mL). The organic layer was dried over anhydrous sodium sulfate. The solvent was evaporated under reduced pressure, 2-propanol was added to the residue and the mixture was stirred at 50° C. for 1 hr. After cooling, the solid was washed with cold 2-propanol (600 mL) and hexane, and dried. 2-Propanol/ethyl acetate (800 mL/80 mL) was added, and the mixture was stirred at 50° C. for 1 hr. After cooling, the solid was washed with cold 2-propanol and hexane, and dried to give the object 4-tert-butyl-N-(4-chloro-2-isonicotinoylphenyl)benzenesulfonamide (162 g, pale-yellow solid). The filtrate was purified by silica gel column chromatography (ethyl acetate/chloroform) to give the object 4-tert-butyl-N-(4-chloro-2-isonicotinoylphenyl)benzenesulfonamide (29 g, pale-yellow solid). A total of 191 g of the object product 4-tert-butyl-N-(4-chloro-2-isonicotinoylphenyl)benzenesulfonamide was obtained.

$^1$H NMR (400 MHz, CDCl$_3$) δ 1.24 (9H, s), 7.20-7.30 (3H, m), 7.39 (2H, d, J=8.6 Hz), 7.55-7.6 (1H, m), 7.67 (2H, d, J=8.6 Hz), 7.81 (1H, d J=8.9 Hz), 8.77 (2H, dd, J=1.5, 4.4 Hz), 10.10 (1H, s).

Synthesis of 4-tert-butyl-N-[4-chloro-2-(1-oxidoisonicotinoyl)phenyl]benzenesulfonamide (compound B)

To a solution of 4-tert-butyl-N-(4-chloro-2-isonicotinoylphenyl)benzenesulfonamide (191 g) in dichloromethane (3000 mL) was added m-chloroperbenzoic acid (65%, 146 g) at 0° C., and the mixture was stirred for 30 min. The mixture was warmed to room temperature and stirred for 16 hr. The mixture was cooled to 0° C., 10% aqueous sodium dithionite solution (630 mL) was added, and the mixture was stirred for 30 min and extracted with chloroform. The organic layer was washed with saturated aqueous sodium hydrogen carbonate solution (500 mL) and saturated brine (500 mL). The organic layer was dried over anhydrous sodium sulfate. The solvent was evaporated under reduced pressure, and purified by silica gel column chromatography (NH, chloroform) to give the object 4-tert-butyl-N-[4-chloro-2-(1-oxidoisonicotinoyl)phenyl]benzenesulfonamide (181 g, pale-yellow solid).

$^1$H NMR (400 MHz, CDCl$_3$) δ 1.24 (9H, s), 7.26-7.45 (5H, m), 7.48-7.58 (1H, m), 7.65 (2H, d, J=8.6 Hz), 7.70-7.82 (1H, m), 8.19 (2H, d, J=7.2 Hz), 9.61 (1H, s).

Synthesis of sodium [(4-tert-butylphenyl)sulfonyl] [4-chloro-2-(1-oxidoisonicotinoyl)phenyl]azanide (Sodium Salt of Compound B)

Sodium hydride (60%, 5.97 g) was washed 3 times with dehydrated hexane (30 mL), dehydrated dimethylformamide (31 mL) was added, and a suspension of 4-tert-butyl-N-[4-chloro-2-(1-oxidoisonicotinoyl)phenyl]benzenesulfonamide (61.0 g) in dehydrated dimethylformamide (300 ml) was added at 0° C. The mixture was warmed to room temperature, and stirred for 3.5 hr. The mixture was filtered, washed with dehydrated dimethylformamide, diluted with dichloromethane (DCM) (2700 mL) and stirred for 20 hr. The solid was filtered, and washed with dichloromethane (500 mL). The reaction was performed twice under similar conditions, and dichloromethane (400 mL) was added to the obtained 3 batches of solid. The mixture was filtered, washed twice with dichloromethane (100 mL) and dried at 50° C. to give a yellow solid (139 g). Toluene (1390 mL) was added to the solid, and the mixture was heated to 60° C., ethanol (1250 mL) was slowly added, and the mixture was stirred at 80° C. for 1 hr. After cooling to room temperature, the solid was filtered, washed twice with toluene/ethanol (9/1, 200 mL), twice with toluene (200 mL), and 4 times with hexane (300 mL), and dried at 50° C. to give the object sodium [(4-tert-butylphenyl)sulfonyl][4-chloro-2-(1-oxidoisonicotinoyl) phenyl]azanide (128 g, yellow solid).

MS: [M+H]$^+$ 445.1.

$^1$H NMR (400 MHz, DMSO-d$_6$) δ 1.27 (9H, s), 6.96 (1H, s), 7.00-7.12 (1H, m), 7.25 (1H, d, J=8.9 Hz), 7.93 (6H, m), 8.15 (2H, d, J=6.8 Hz).

Anal. Calcd for C$_{22}$H$_{20}$ClN$_2$O$_4$SNa: C, 56.59; H, 4.32; N, 6.00; S, 6.87; Cl, 7.59. Found: C, 56.20; H, 4.29; N, 5.95; S, 6.50; Cl, 7.64.

Formulation Example 1

Compound A, mannitol and crystalline cellulose were uniformly mixed in a fluid bed dryer granulator (FD-5S, POWREX) according to the formulation of Table 1, and granulated by spraying an aqueous solution of hydroxypropylcellulose in the granulator and dried therein. The obtained granules were sieved by a screening mill (P-3, Showa Kagaku Kikai Co., Ltd.) to give a sieved powder. To the sieved powder were added croscarmellose sodium and magnesium stearate, and they were mixed in a diffusion type blending machine (60 L, Showa Kagaku Kikai Co., Ltd.) to give granules for tableting. The granules were tableted by a rotary tableting machine (Aquarius, Kikusui Seisakusho Ltd.) with a punch of 16×9 mm to give core tablets each weighing 600 mg. A solution containing hypromellose2910, macrogol6000, titanium oxide, red ferric oxide and yellow ferric oxide was sprayed on the obtained core tablets in a film coating machine (Driacoater650, POWREX) to give film-coated tablets each containing compound A (2 mg or 10 mg or 100 mg or 200 mg) per tablet.

TABLE 1

|  | 2 mg | 10 mg | 100 mg | 200 mg |
| --- | --- | --- | --- | --- |
| Compound A | 2 | 10 | 100 | 200 |
| mannitol | 484 | 476 | 386 | 286 |
| crystalline cellulose | 60 | 60 | 60 | 60 |
| hydroxypropylcellulose | 18 | 18 | 18 | 18 |
| croscarmellose sodium | 30 | 30 | 30 | 30 |
| magnesium stearate | 6 | 6 | 6 | 6 |
| hypromellose2910 | 18 | 18 | 18 | 18 |
| macrogol6000 | 4 | 4 | 4 | 4 |
| titanium oxide | 2 | 2 | 2 | 2 |
| red ferric oxide | 0.133 | 0.133 | 0.133 | 0.133 |
| yellow ferric oxide | 0.267 | 0.267 | 0.267 | 0.267 |
| total | 624.4 | 624.4 | 624.4 | 624.4 |

Experimental Example 1

Analysis of CCR9 mRNA Expression Level of Peripheral Blood Cell of Sjogren's Syndrome Patients (Patients and Control Individuals)

Using the whole blood frozen after collecting from 5 patients (Caucasian family, 46-80 years old) diagnosed with Sjogren's syndrome (Conversant Biologics, Inc.), who consented to the announcement of research use, and the whole blood frozen after collecting from 5 healthy donors randomly selected as a comparison control as study samples, CCR9 expression was analyzed by real-time PCR. This experiment was approved by the research ethics committee established in the research institute, and all samples were provided after ensuring anonymity by the provider.

(Purification of RNA from Frozen Peripheral Blood)

For RNA analysis, the frozen peripheral blood of the Sjogren's syndrome patients and randomly-selected healthy donors was thawed at room temperature, and used as samples for RNA purification. Using NucleoSpin RNA Blood Kit (Macherey-Nagel, Ref #740200.50) and following the manufacturer's instruction manual, the attached Lysis buffer (200 µl) and Proteinase K solution (5 ul) were added to the sample (200 µl) and the mixture was reacted at room temperature for 15 min. Then, 200 µl of 70% ethanol was further added, and the mixture was sufficiently blended, and passed through the attached Nucleospin RNA Blood Column to adsorb RNA to the column. The attached MDB solution (350 µl) was added to said column for desalting washing, the attached rDNase (95 µl) solution was added, and the mixture was reacted at room temperature for 15 min to remove the DNA mixed therein. Using the attached washing buffer, the mixture was washed 3 times to remove impurities, and RNA was finally eluted with 60 µl of RNase-free water.

(Real-Time PCR)

Using the purified RNA as a sample and QuantiTect Probe RT-PCR Kit (Qiagen, Cat #204445) and following the manufacturer's instruction manual, the relative expression level of CCR9 against β-actin, which is an endogenously expressed housekeeping gene, was measured by real-time PCR method. To the 2× QuantiTect Probe RT-PCR Master Mix (10 µl) attached to the QuantiTect Probe RT-PCR Kit were added the attached QuantiTect RT Mix (0.2 µl) and human CCR9 probe (Applied Biosystems, Hs01890924_s1) or human β-actin probe (Applied Biosystems, Part #4326315E) (1 µl, final concentration 1 µM), and further, purified RNA (2 µl) (1 pg-1 µg as RNA amount), RNase-free water (6.8 µl) to adjust the final volume to 20 µl. This sample was subjected to a duplicate experiment (45 cycles of reverse transcription reaction at 50° C. for 20 min, PCR initial activation at 95° C. for 15 min, 2 step cycling (denaturation at 94° C. for 15 sec, annealing extension at 60° C. for 60 sec)) using 7900HT Fast Real-Time PCR System (Applied Biosystems).

(Gene Expression Data Analysis)

The target (mRNA) number was standardized against the endogenously expressed housekeeping gene (β-actin) corresponding to each sample, uncontrolled variability between samples was adjusted and the relative expression level of CCR9 was calculated. The results are shown in FIG. 1. The Sjogren's syndrome patients who are the analysis subject in this experiment showed a clear increase in the CCR9 mRNA expression level of the peripheral blood cells as compared to the healthy individuals.

Experimental Example 2

Effect of Compound a on Saliva Secretion Amount in the Sjogren's Syndrome Animal Model 1. Animal Model As an animal model for Sjogren's syndrome, most widely used NOD/ShiLtJ mouse (hereinafter sometimes referred to as NOD mouse) was selected since it meets the both conditions of the diagnosis standard: 1) development of dry eye and dry mouth, 2) increase of anti-SS-A/Ro and anti-SS-B/La antibody titer, and is easily available (Tegan N. Lavoie et. al., Journal of Biomedicine and Biotechnology Volume 2011 (2011), Article ID 549107, pp 1-14). 6-Week-old NOD mice were purchased from The Jackson Laboratory (US), after acclimatization for 1-2 weeks, animals before onset of diabetes were divided into 3 groups (maximum 30 mice per group) by randomization into each of the groups based on the body weight measured before the start of the test drug administration and the data of saliva secretion amount by pilocarpine stimulation under ketamine•xylazine anesthesia and subjected to the test. During the test drug treatment, the body weight and the blood glucose level were monitored at least once a week. The blood glucose level of several µL of the blood collected from the tail vein under 1-5% isoflurane anesthesia was measured by a blood glucose level measuring instrument (Accu-Chek Aviva Nano, Roche diagnostics K.K.). The diabetes diagnosis criteria was not less than 250 mg/dL, and one insulin pellet (LinBit, LinShin Canada, Inc.) was subcutaneously transplanted under 1-5% isoflurane anesthesia into the abdomen of the mouse that developed diabetes, and the blood glucose was controlled during the study by monitoring the blood glucose level, and adding or removing the pellet as necessary.

2. Administration of Compound A

Compound A was orally administered twice daily (minimum ic dosing interval 6 hours) every day except Saturdays and Sundays. The dose of compound A was 50 mg/kg or 250 mg/kg, and 0.2 mL was orally administered as a single dose. The concentration of compound A was appropriately controlled by calculating an average body weight of the group once a week from the body weights of the NOD mice, and adjusting the concentration such that the administration of 0.2 mL results in the administration of each dose. On the other hand, the vehicle group without administration of compound A was orally administered with 0.2 mL of 0.5% methylcellulose solution in the same schedule as above.

3. Measurement of Saliva Secretion Amount

Under anesthesia by intraperitoneal administration of a mixture (10 mL/kg) of ketamine (100 mg/kg) and xylazine (10 mg/kg), the saliva secreted in 15 min after subcutaneous administration of pilocarpine (5 mg/kg) was collected with defatted cotton, and the secretion amount was calculated from the defatted cotton weight before and after the measurement.

Figure 2:
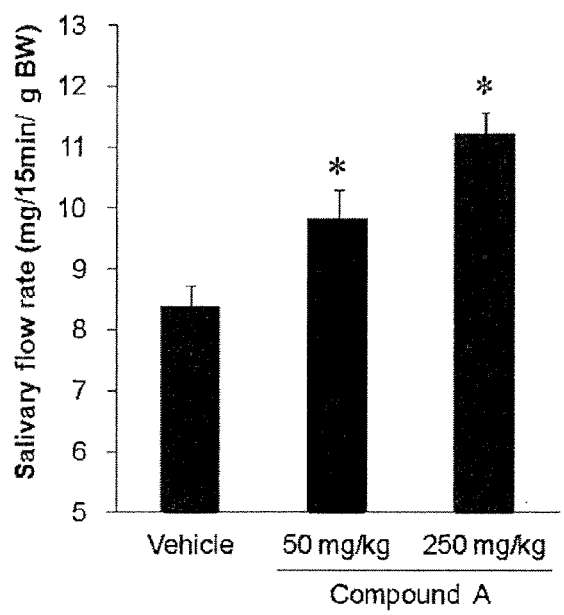
FIG. 2 shows the results of Experimental Example 2, wherein saliva secretion amounts of Sjogren's syndrome animal model administered with compound A from 8-week-old to 21-week-old are shown.
Figure 3:
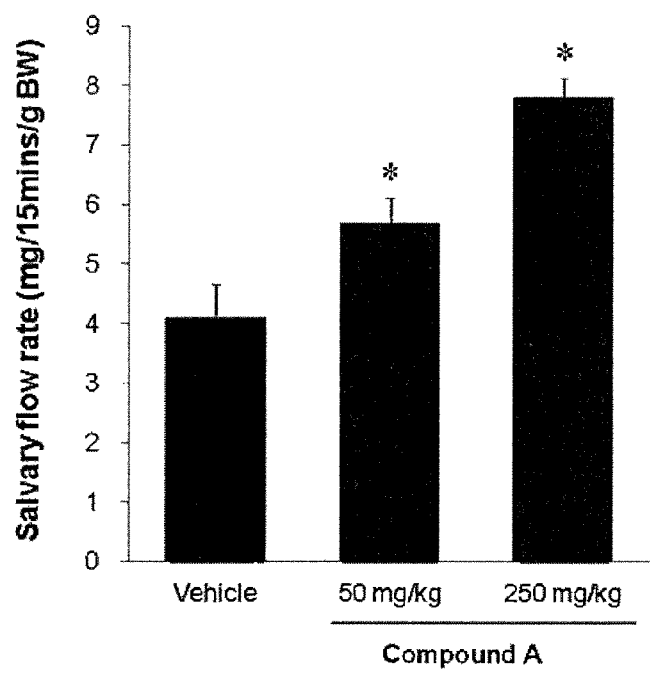
FIG. 3 shows the results of Experimental Example 2, wherein saliva secretion amounts of Sjogren's syndrome animal model administered with compound A from 8-week-old to 26-week-old are shown.

This measurement was performed twice when the mice reached 21-week-old and 26-week-old. The results are shown in FIG. 2 and FIG. 3.

4. Saliva Secretion Amount in 21-Week-Old NOD Mouse

The saliva secretion amount of the vehicle group decreased with the onset of diabetes, and decreased to about 8.3 (mg/15 min/g BW) at the time point of 21-week-old. In contrast, the 50 mg/kg compound A treatment group and the 250 mg/kg compound A treatment group showed a statistically significant high value of about 9.8 (mg/15 min/g BW) and about 11.2 (mg/15 min/g BW), respectively (FIG. 2).

5. Saliva Secretion Amount in 26-Week-Old NOD Mouse

The saliva secretion amount of the vehicle group decreased to about 4.0 (mg/15 min/g BW). On the other hand, the 50 mg/kg compound A treatment group and the 250 mg/kg compound A treatment group showed a statistically significant high value of about 5.5 (mg/15 min/g BW) and about 8.0 (mg/15 min/g BW), respectively. Particularly, the 250 mg/kg compound A treatment group showed a two-fold increase of saliva secretion amount than the vehicle group (FIG. 3).

From these results, it was shown that compound A treatment significantly suppressed a decrease in the saliva secretion amount in a dose-dependent manner in the NOD mouse, that is, it improved Sjogren's syndrome-like symptoms.

Experimental Example 3

Figure 4:
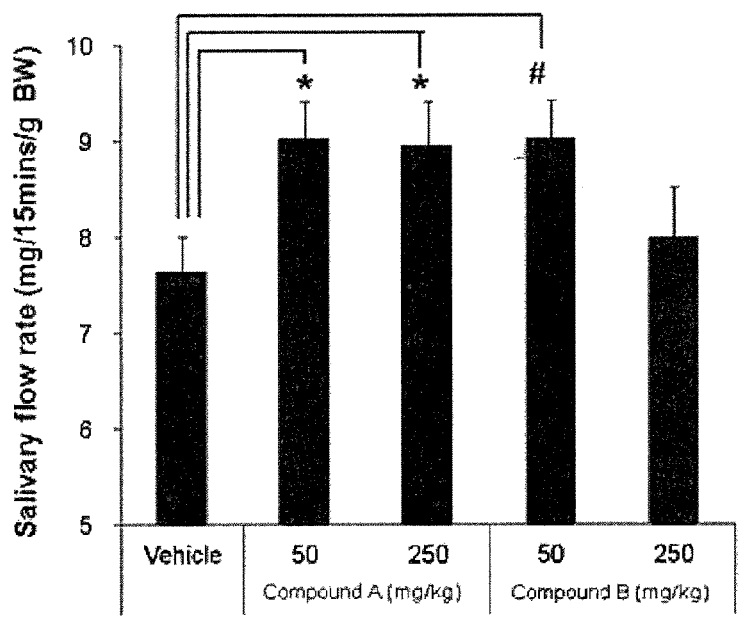
FIG. 4 shows the results of Experimental Example 3, wherein saliva secretion amounts of Sjogren's syndrome animal model administered with compound A or compound B from 8-week-old to 23-week-old are shown.

Effect of Compounds a and B on Saliva Secretion Amount in Sjogren's Syndrome Animal Model The saliva secretion amount in 23-week-old NOD mice administered with compound A or compound B was measured in the same manner as in Experimental Example 2. The results are shown in FIG. 4.

In compound A treatment groups at 50 mg/kg and 250 mg/kg, both doses significantly suppressed a decrease in the saliva secretion amount with sufficient reproducibility. On the other hand, in the compound B treatment group, the saliva secretion amount from treatment group was significantly higher at 50 mg/kg as compared to the vehicle group, but the dose-dependent effect was not found. The tolerability in this efficacy study for a relatively long term using the same dose range was clearly superior with compound A to compound B.

Experimental Example 4

Figure 5:
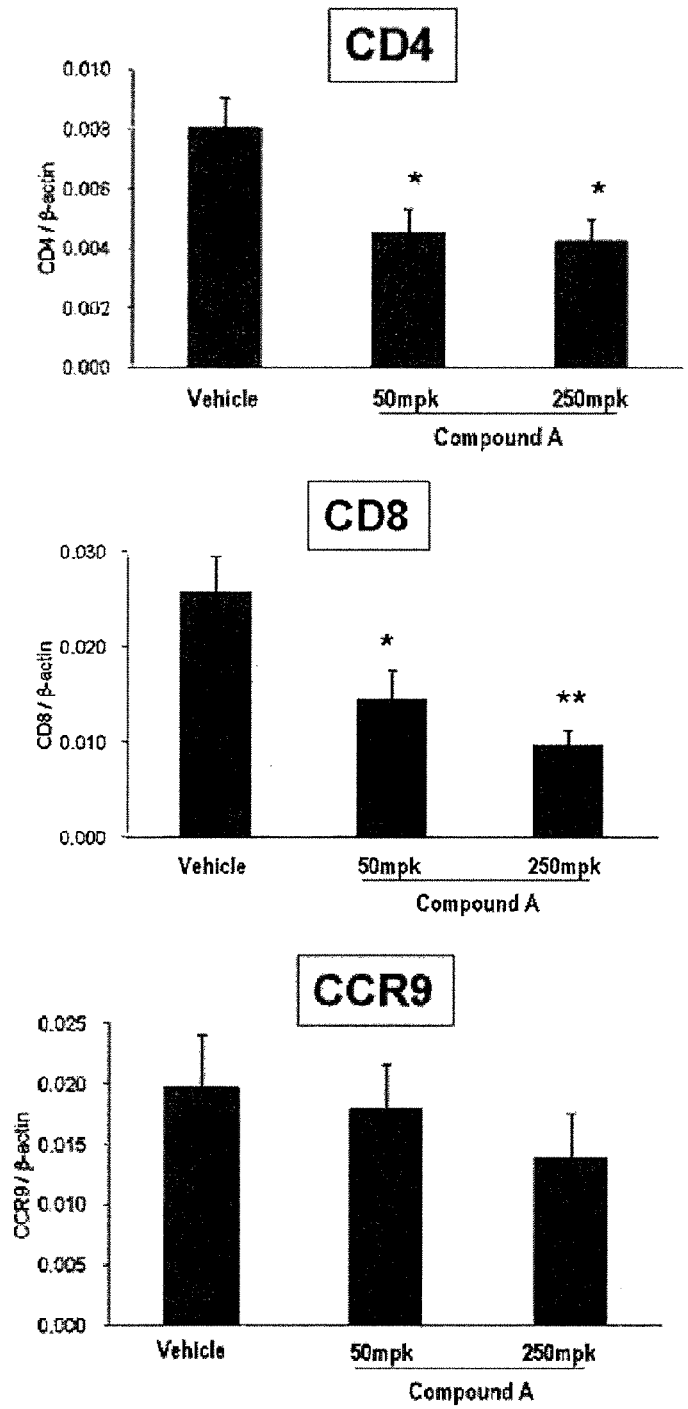
FIG. 5 shows the results of Experimental Example 4, wherein mRNA expression levels of CD4+ T cells, CD8+ T cells and CCR9 in salivary gland tissues of Sjogren's syndrome animal model administered with compound A from 8-week-old to 26-week-old are shown.

Variation in mRNA Expression Level of CD4+ T Cells, CD8+ T Cells and CCR9 in Salivary Gland Tissues when Compound A was Orally Administered to Sjogren's Syndrome Animal Model The salivary gland of the 26-week-old NOD mice used in Experimental Example 2 for the measurement of the saliva secretion amount was removed, the total RNA was recovered from there, and the mRNA levels of CD4, CD8 and CCR9 were normalize with the β-actin expression level as the internal standard. The results are shown in FIG. 5.

The amount of CD4+ T cells in the salivary gland decreased to about half in the compound A treatment group as compared to the vehicle group. In addition, the amount of CD8+ T cells in the salivary gland decreased to about half in the 50 mg/kg compound A treatment group and to about one-third in the 250 mg/kg compound A treatment group, in a dose-dependent manner as compared to the vehicle group. The mRNA expression level of CCR9 in the salivary gland tended to decrease in a dose-dependent manner in the compound A treatment group as compared to the vehicle group.

From these results, it was shown that the amounts of CD4+ T cells and CD8+ T cells, which are inflammatory lymphocytes that infiltrate into the salivary gland tissue, were suppressed by the treatment of compound A. That is, it was suggested that compound A maintains the function of saliva secretion by suppressing the infiltration of inflammatory cells that both attack and destroy the salivary gland tissues.

Experimental Example 5

Figure 6:
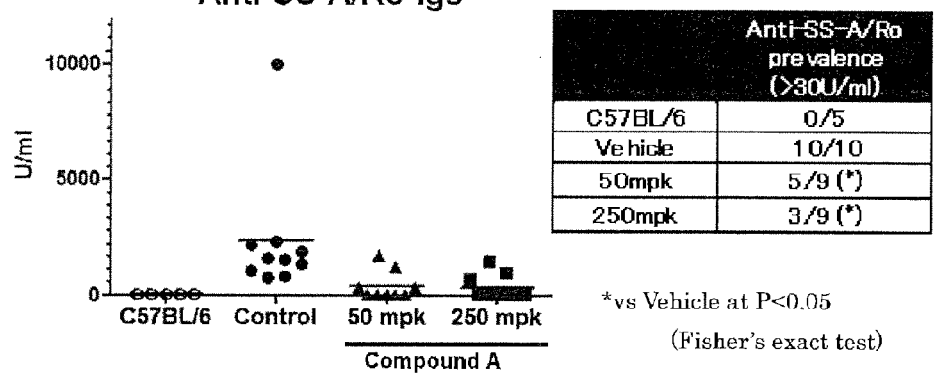
FIG. 6 shows the results of Experimental Example 5, wherein antibody titers of anti-SS-A/Ro antibody and anti-SS-B/La antibody in blood of Sjogren's syndrome animal model administered with compound A from 8-week-old to 26-week-old are shown.
Figure 6:
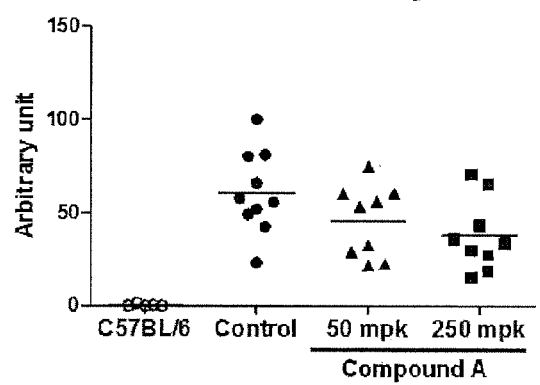

Variation of Antibody Titer of Anti-SS-A/Ro Antibody and Anti-SS-B/La Antibody in Blood of Sjogren's Syndrome Animal Model Orally Administered with Compound A Blood samples from the 26-week-old NOD mice used in Experimental Example 2 for the measurement of the saliva secretion amount were collected, and ELISA test was carried out for two subsets of anti-SS-A/Ro and anti-SS-B/La found commonly in Sjogren's syndrome. The results are shown in FIG. 6.

1) Anti-SS-B/La IgG ELISA
antigen: SS-B (RayBiotech, Inc., MD-27-0019P)
plate: Immuno 96 Microwell Plate (Nunc, 442404)
washing: 0.1% Tween 20 containing PBS (hereinafter sometimes to be referred to as PBS/T)
substrate: One tablet of o-phenylenediamine dihydrochloride (OPD) (Sigma, P-4809) was dissolved in 50 mM citric acid-phosphoric acid buffer pH 5.0 (Sigma, P-4809) (10 mL), and 4 μL aqueous hydrogen peroxide was added.
SS-A and SS-B were each diluted with 50 mM carbonate buffer pH 9.6 (Sigma, C-3041) to 0.5 μg/mL and 1.0 μg/mL, respectively, and the antigen was added to an ELISA plate at 50 μL/well. After incubation at 4° C. overnight, the plate was washed 3 times with PBS/T, added with 2% BSA in PBS at 200 μL/well, and incubated at room temperature for 1 hr. After washing once with PBS/T, the serum diluted with PBS/T (100- to 500-fold) was added at 50 μL/well, and the mixture was incubated at room temperature for 1-2 hr. Thereafter, it was washed 5 times with PBS/T, added with diluted peroxidase labeled anti-mouse IgG antibody (H&L) at 50 μL/well, and the mixture was incubated at room temperature for 1 hr, added with the antibody diluted with PBS/T and incubated at room temperature for 1 hr. After washing 5 times with PBS/T, an enzyme substrate solution was added at 50 μL/well, and 2N sulfuric acid was added at 50 μL/well 10-30 min later to quench the reaction.

2) Anti-SS-A/Ro Ig ELISA
For quantification of the Total Anti-SSA Ig (IgG+IgA+IgM) in the serum, commercially available Mouse Anti-SSA Total Ig ELISA Kit Cat. No. 5710 (manufactured by ALPHA DIAGNOSTIC INTERNATIONAL) was used. The standard protocol was partly modified. A mouse serum sample was diluted 1/10-fold, the serum of C57BL/6 mouse was added to anti-SSA calibrator solution (Calibrator solution) to give 10% serum.

Both blood anti-SS-A/Ro antibody (anti-SS-A/Ro Igs) and anti-SS-B/La antibody (anti-SS-B/La IgG) are autoantibodies that show an increased antibody titer in patients who developed Sjogren's syndrome, and used as diagnostic markers. The antibody titer scarcely increased in the C57BL/6 mouse used as a control animal without salivary dysfunction, whereas NOD mouse in the vehicle group showed a remarkable increase in the antibody titer. The remarkably increased antibody titer decreased in a dose-dependent manner by the treatment of compound A, and particularly, anti-SS-A/Ro antibody was suppressed to the control level in about 70% of the 250 mg/kg compound A treatment group, thus exhibiting a remarkable decreasing effect against useful diagnostic markers for Sjogren's syndrome.

When the antibody titer is not less than 30 Unit, positive anti-SS-A/Ro is diagnosed as one of the classification criteria for Sjogren's syndrome. While the vehicle group showed 100% onset, compound A treatment group significantly suppressed the onset frequency as demonstrated by about 50% onset in the 50 mg/kg treatment group and about 30% onset in the 250 mg/kg treatment group.

From these results, it was shown that compound A treatment suppressed an increase in the antibody titer, which is a diagnostic marker of Sjogren's syndrome, in a dose-dependent manner, and prevented the disease progression.

Experimental Example 6

Time-Course Changes in Concentration of Compound A and Compound B in Plasma in Sjogren's Syndrome Animal Model (Administration of Compound)
The compound was orally administered twice per day to 8-week-old NOD mouse under the following conditions, and administration was repeated for 19 weeks.

| | |
|---|---|
| Food intake | non-fasting |
| dose | 50 mg/kg, 250 mg/kg |
| administration medium | 0.5% methylcellulose solution |
| administration time | 0, 8 hr |
| plasma collection time | first group: 0.25, 1, 4, 8.25, 9, 12, 24 hr |
| | second group: pre(0), 0.5, 2, 8, 8.5, 10, 16 hr |

(Pre-Treatment of Plasma)

To the plasma (5 μL) collected from the NOD mouse were added a solvent solution (dimethyl sulfoxide/acetonitrile (2:8), 5 μL), and compound A solution (compound A dissolved in solvent solution, 5 μL) or compound B solution (compound B dissolved in solvent solution, 5 μL) for drawing an analytical curve. An internal standard substance (acetonitrile (115 μL) containing a deuterated form of compound A, or diclofenac sodium, 100 ng/mL)) was added, and the mixture was vigorously stirred. The mixture was centrifuged at 5250 rpm. To the supernatant (30 μL) was added a dilution solvent (60 μL) to give a sample solution (mobile phase A:mobile phase B=9:1 (v/v) was used as a dilution solvent).

(Plasma Analysis)

The above-mentioned sample solution was injected into an HPLC-MS/MS analysis apparatus, and the obtained peak area was converted to concentration from the analytical curve. The detail of the analysis apparatus is shown below.

HPLC Conditions

| system | Ultra high-performance liquid chromatography (UFLC) |
|---|---|
| column | Shimadzu Shim-pack XR-ODS (2.2 μm, 2.0 × 30 mm) |
| mobile phase A | 10 mmol/L ammonium formate/formic acid (100: 0.2, v/v) |
| mobile phase B | acetonitrile/formic acid (100: 0.2, v/v) |
| flow rate | 0.7 mL/min |
| column temperature | 50° C. |
| injection volume | 2 μL |

Mobile Phase Gradient Conditions

TABLE 2

| time (min) | concentration (%) of mobile phase B |
|---|---|
| 0.00 | 5 |
| 0.20 | 5 |
| 1.30 | 99 |
| 2.00 | 99 |
| 2.01 | 5 |
| 2.60 | 5 |

MS Conditions

| system | API5000 |
|---|---|
| ionization mode | turbo ion spray |
| ion polarity mode | positive |
| scan mode | selective reaction detection method (SRM) |

Figure 7:
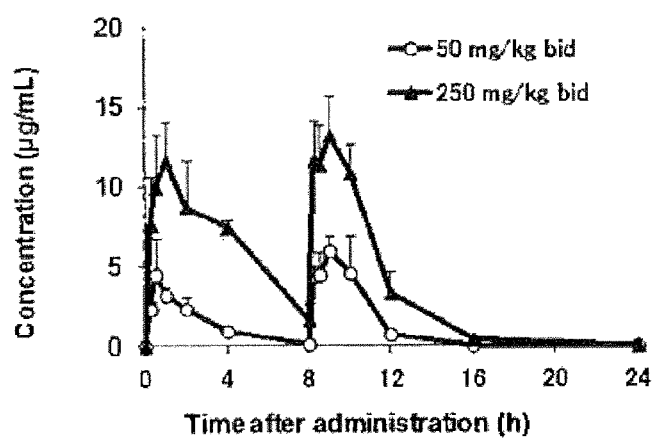
FIG. 7 shows the results of Experimental Example 6, wherein time-course changes in the plasma concentration of Sjogren's syndrome animal model repeatedly administered with compound A for 19 weeks are shown.
Figure 8:
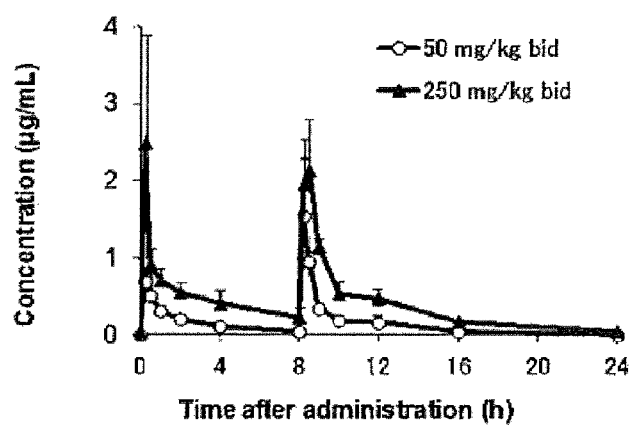
FIG. 8 shows the results of Experimental Example 6, wherein time-course changes in the plasma concentration of Sjogren's syndrome animal model repeatedly administered with compound B for 19 weeks are shown.

The results are shown in FIG. 7 and FIG. 8.

Compound A was rapidly metabolized without accumulation in the body, and showed good blood exposure (FIG. 7). Similarly, compound B was also rapidly metabolized without accumulation in the body. However, its AUC was about one-tenth that of compound A (FIG. 8).

This application is based on U.S. provisional patent application Nos. 61/733,176 and 61/894,641, the contents of which are incorporated in full herein.

The invention claimed is:

1. A method for the treatment of Sjogren's syndrome, comprising administering an effective amount of a compound represented by the formula (I):

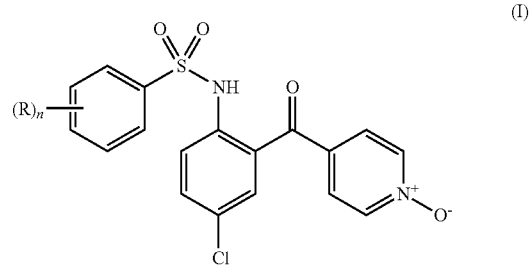

(I)

wherein n is an integer of 1-3;

R is each independently an aliphatic group, haloalkyl, aryl, arylalkyl, alkoxy, cycloalkoxy, haloalkoxy, aryloxy, arylalkoxy, alkylthio, a halogen atom, nitro, cyano, hydroxy, $NR^1CO_2R^2$, $C(O)N(R^1)_2$, $C(O)R^2$, $CO_2R^2$, $OC(O)N(R^1)_2$, $OC(O)R^2$, $N(R^1)_2$ or $NR^1C(O)R^2$; or two adjacent R groups form, together with an atom bonded thereto, a condensed, saturated, unsaturated, or partially unsaturated 5- to 7-membered ring having 0, 1 or 2 hetero atoms selected from N, O and S;

$R^1$ is each independently a hydrogen atom or an aliphatic group; and $R^2$ is an aliphatic group, or a pharmaceutically acceptable salt thereof, to a subject in need thereof.

2. The method according to claim 1, wherein R is an aliphatic group, alkoxy or haloalkoxy.

3. The method according to claim 1, wherein the compound represented by the formula (I) is N-{4-chloro-2-[(1-oxidopyridin-4-yl)carbonyl]phenyl}-4-(propan-2-yloxy)benzenesulfonamide.

4. The method according to claim 1, wherein the compound represented by the formula (I) is N-{4-chloro-2-[(1-oxidopyridin-4-yl)carbonyl]phenyl}-4-(tert-butyl)benzenesulfonamide.

* * * * *

UNITED STATES PATENT AND TRADEMARK OFFICE
CERTIFICATE OF CORRECTION

PATENT NO. : 8,815,887 B2
APPLICATION NO. : 14/095026
DATED : August 26, 2014
INVENTOR(S) : Suzuki et al.

It is certified that error appears in the above-identified patent and that said Letters Patent is hereby corrected as shown below:

On the Title Page:

(Item 71) delete "Takeda Pharmaceutical Company Limited" and insert --Millennium Pharmaceuticals, Inc.--.

(Item 73) delete "Millenium Pharmaceuticals, Inc." and insert --Millennium Pharmaceuticals, Inc.--.

In the Specification:

Col. 6, line 29, delete "is".

Col. 8, line 58, delete "include aspartic acid" and insert --include salts with aspartic acid--.

Col. 9, line 20, delete "chiblain" and insert --chilblain--.

Col. 9, line 23, delete "faciej" and insert --faciei--.

Col. 10, lines 31-32, delete "hydroxyethylcellulocse" and insert --hydroxyethylcellulose--.

Col. 16, line 19, delete "53.38" and insert --δ3.38--.

Col. 16, delete "Step 3" from line 58, and insert --Step 3-- at line 26.

Col. 20, line 35, delete "1800 r" and insert --1800 mL--.

Col. 24, line 18, delete "ic".

Col. 24, line 61, delete "a" and insert --A--.

Signed and Sealed this
Fifteenth Day of September, 2015

Michelle K. Lee
*Director of the United States Patent and Trademark Office*